(12) United States Patent
Wagner et al.

(10) Patent No.: US 11,584,937 B2
(45) Date of Patent: Feb. 21, 2023

(54) COMPOSITIONS AND METHODS FOR CONTROLLING PLANT GROWTH AND DEVELOPMENT

(71) Applicant: THE TRUSTEES OF THE UNIVERSITY OF PENNSYLVANIA, Philadelphia, PA (US)

(72) Inventors: Doris Wagner, Narberth, PA (US); Nobutoshi Yamaguchi, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 56 days.

(21) Appl. No.: 15/307,356

(22) PCT Filed: Apr. 28, 2015

(86) PCT No.: PCT/US2015/027993
§ 371 (c)(1),
(2) Date: Oct. 27, 2016

(87) PCT Pub. No.: WO2015/168124
PCT Pub. Date: Nov. 5, 2015

(65) Prior Publication Data
US 2017/0058284 A1    Mar. 2, 2017

Related U.S. Application Data

(60) Provisional application No. 61/985,315, filed on Apr. 28, 2014.

(51) Int. Cl.
*C12N 15/82* (2006.01)
*C07K 14/415* (2006.01)
*C12N 9/02* (2006.01)

(52) U.S. Cl.
CPC .......... *C12N 15/827* (2013.01); *C07K 14/415* (2013.01); *C12N 9/0071* (2013.01); *C12N 15/8223* (2013.01); *C12N 15/8243* (2013.01); *C12Y 114/11* (2013.01)

(58) Field of Classification Search
None
See application file for complete search history.

(56) References Cited

U.S. PATENT DOCUMENTS

| | | |
|---|---|---|
| 5,015,580 A | 5/1991 | Christou et al. |
| 5,538,880 A | 7/1996 | Lundquist et al. |
| 5,550,318 A | 8/1996 | Adams et al. |
| 5,591,616 A | 1/1997 | Hiei et al. |
| 5,635,055 A | 6/1997 | Sweet et al. |
| 5,824,877 A | 10/1998 | Hinchee et al. |
| 5,981,840 A | 11/1999 | Zhao et al. |
| 6,160,208 A | 12/2000 | Lundquist et al. |
| 6,384,301 B1 | 5/2002 | Martinell et al. |
| 6,399,861 B1 | 6/2002 | Anderson et al. |
| 6,403,865 B1 | 6/2002 | Koziel et al. |
| 2003/0028913 A1 | 2/2003 | Hein et al. |
| 2003/0196219 A1 | 10/2003 | Zhang |
| 2007/0079396 A1 | 4/2007 | Malvar et al. |
| 2007/0149401 A1 | 6/2007 | Haskell et al. |
| 2008/0307541 A1 | 12/2008 | Hsieh |
| 2009/0313725 A1* | 12/2009 | Yu .................. C12N 9/0071 800/290 |
| 2010/0199371 A1 | 8/2010 | Castle et al. |
| 2011/0113514 A1 | 5/2011 | Malvar et al. |
| 2011/0209247 A1 | 8/2011 | Aharoni et al. |

FOREIGN PATENT DOCUMENTS

| | | |
|---|---|---|
| WO | WO 2004/035797 A2 | 4/2004 |
| WO | WO2004035797 A2 * | 4/2004 |
| WO | WO 2013/186038 A1 | 12/2013 |

OTHER PUBLICATIONS

Zhang, et al. The Plant Journal 67.2 (2011): 342-353. (Year: 2011).*
Jia, et al. Functional & integrative genomics 9.2 (2009): 255-262. (Year: 2009).*
Blazquez et al. (Development 124, 3835-3844 (1997)). (Year: 1997).*
Krizek et al. (Sexual plant reproduction 12.1 (1999): 14-26). (Year: 1999).*
Spinelli et al. (Plant physiology 156.4 (2011): 1894-1904). (Year: 2011).*
Blázquez et al. (Nature 404.6780 (2000): 889). (Year: 2000).*
Ahearn et al. (Plantand Cell Physiology 42.10 (2001): 1130-1139). (Year: 2001).*
Sun (Current opinion in plant biology 3.5 (2000): 374-380). (Year: 2000).*
Comelli et al. "Founder-cell-specific transcription of the DORNRÖSCHEN-LIKE promoter and integration of the auxin response." Journal of Experimental Botany 67.1 (2016): 143-155. (Year: 2016).*
Shahmuradov, et al. (Nucleic acids research 45.8 (2017): e65-e65). (Year: 2017).*
Yu et al. "Temporaral Control of Trichome Distribution by MicroRNA 156-Targeted SPL Genes in *Arabidopsis thaliana*."The Plant Cell, Jul. 9, 2010, vol. 2, pp. 2322-2355.

* cited by examiner

*Primary Examiner* — Charles Logsdon
(74) *Attorney, Agent, or Firm* — Mark S. Cohen; Pearl Cohen Zedek Latzer Baratz LLP

(57) ABSTRACT

The invention relates to molecules for controlling plant growth and development. Specifically, the invention relates to molecules comprising a gibberellin activator or a gibberellin inhibitor operably linked to a promoter specific to a lateral organ primordium. The invention also relates to transgenic plants having the transgenic molecules and methods for making such transgenic plants.

2 Claims, 14 Drawing Sheets
Specification includes a Sequence Listing.

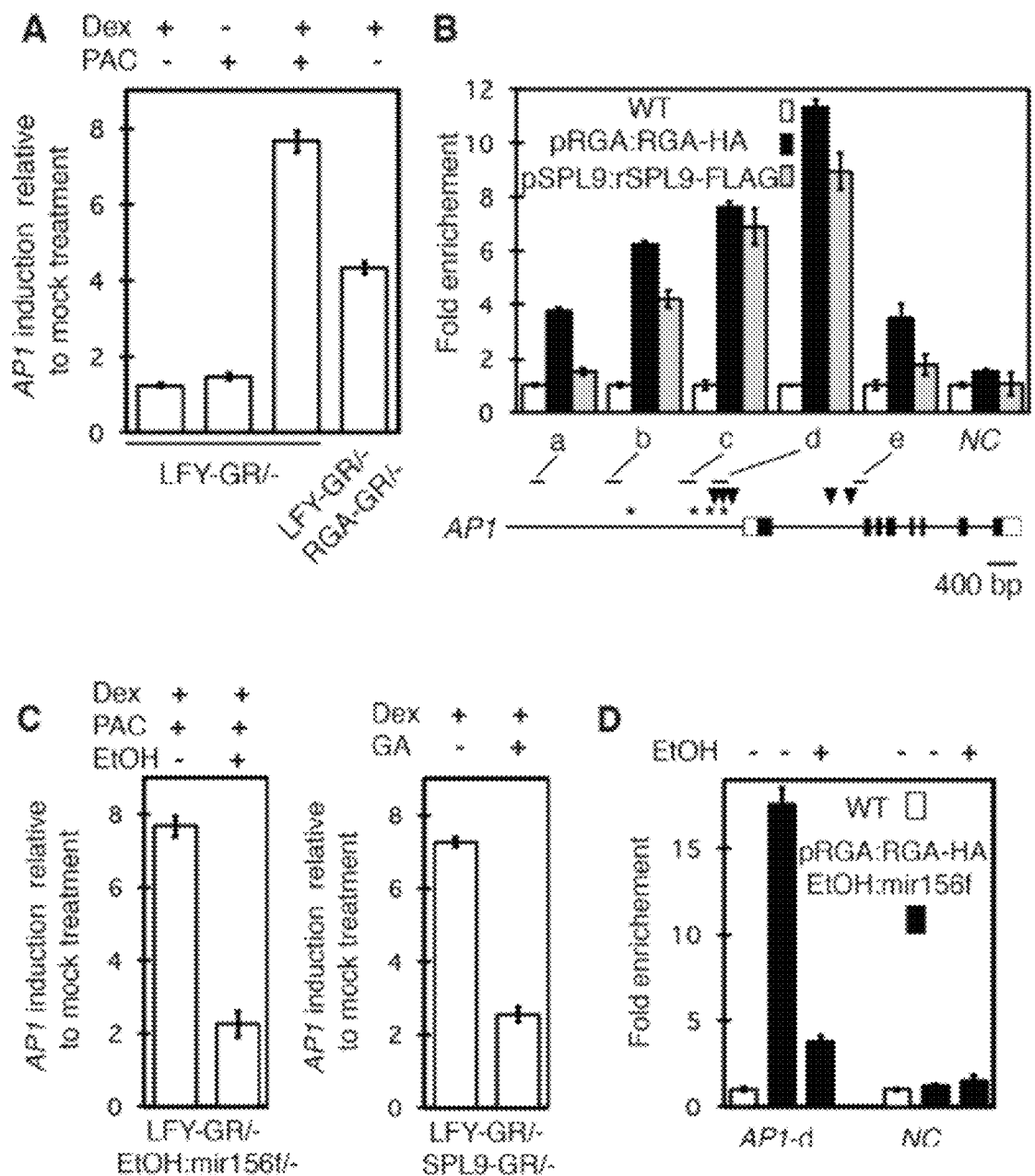
FIGURE 4 (4A-4D)

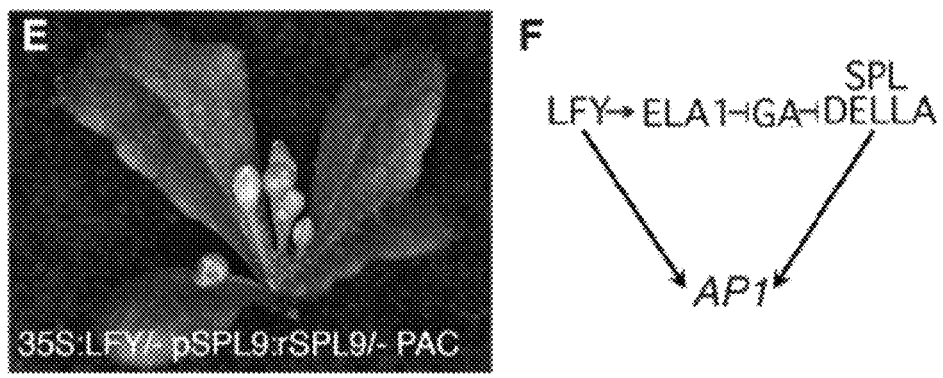
FIGURE 4 (4E-4F)

```
                    SEQUENCE LISTING

<160> NUMBER OF SEQ ID NOS: 60

<210> SEQ ID NO 1
<211> LENGTH: 21
<212> TYPE: DNA
<213> ORGANISM: Artificial Sequence
<220> FEATURE:
<223> OTHER INFORMATION: Primary LFY binding motif

<400> SEQUENCE: 1
tttctatctt tcggtccctc t                                              21

<210> SEQ ID NO 2
<211> LENGTH: 21
<212> TYPE: DNA
<213> ORGANISM: Artificial Sequence
<220> FEATURE:
<223> OTHER INFORMATION: Primary LFY binding motif

<400> SEQUENCE: 2
gtatggaccg atagacaaat t                                              21

<210> SEQ ID NO 3
<211> LENGTH: 13
<212> TYPE: DNA
<213> ORGANISM: Artificial Sequence
<220> FEATURE:
<223> OTHER INFORMATION: Secondary LFY binding motif

<400> SEQUENCE: 3
ggaccgatag aca                                                       13

<210> SEQ ID NO 4
<211> LENGTH: 13
```

<212> TYPE: DNA
<213> ORGANISM: Artificial Sequence
<220> FEATURE:
<223> OTHER INFORMATION: Secondary LFY binding motif

<400> SEQUENCE: 4
agcccatgtg tct                                                    13

<210> SEQ ID NO 5
<211> LENGTH: 50
<212> TYPE: DNA
<213> ORGANISM: Artificial Sequence
<220> FEATURE:
<223> OTHER INFORMATION: pELA1/gELA-FW primer

<400> SEQUENCE: 5
ggggacaagt ttgtacaaaa aagcaggcta cagaaacagc aagagctttt           50

<210> SEQ ID NO 6
<211> LENGTH: 51
<212> TYPE: DNA
<213> ORGANISM: Artificial Sequence
<220> FEATURE:
<223> OTHER INFORMATION: pELA1-RV primer

<400> SEQUENCE: 6
ggggaccact ttgtacaaga aagctgggtt tttcttatct ttcttttct t          51

<210> SEQ ID NO 7
<211> LENGTH: 51
<212> TYPE: DNA
<213> ORGANISM: Artificial Sequence
<220> FEATURE:
<223> OTHER INFORMATION: gELA1/ELA1ox-RV primer

<400> SEQUENCE: 7
ggggaccact ttgtacaaga aagctgggtt atattgtctc agaactctaa t         51

<210> SEQ ID NO 8
<211> LENGTH: 50
<212> TYPE: DNA
<213> ORGANISM: Artificial Sequence
<220> FEATURE:
<223> OTHER INFORMATION: ELA1ox-FW primer

<400> SEQUENCE: 8
ggggacaagt ttgtacaaaa aagcaggcta catggagaat tttatggtag           50

<210> SEQ ID NO 9
<211> LENGTH: 20
<212> TYPE: DNA
<213> ORGANISM: Artificial Sequence
<220> FEATURE:
<223> OTHER INFORMATION: pLFY-FW primer

<400> SEQUENCE: 9
ggatccattt ttcgcaaagg                                             20

<210> SEQ ID NO 10
<211> LENGTH: 20
<212> TYPE: DNA
<213> ORGANISM: Artificial Sequence
<220> FEATURE:
<223> OTHER INFORMATION: pLFY-RV primer

<400> SEQUENCE: 10

```
aatctatttt tctctctctc                                                    20

<210> SEQ ID NO 11
<211> LENGTH: 26
<212> TYPE: DNA
<213> ORGANISM: Artificial Sequence
<220> FEATURE:
<223> OTHER INFORMATION: RGL1/rgl1-FW primer

<400> SEQUENCE: 11
ctgcagatga agagagagca caacca                                             26

<210> SEQ ID NO 12
<211> LENGTH: 26
<212> TYPE: DNA
<213> ORGANISM: Artificial Sequence
<220> FEATURE:
<223> OTHER INFORMATION: RGL1/rgl1-RV primer

<400> SEQUENCE: 12
gtcgacttat tccacacgat tgattc                                             26

<210> SEQ ID NO 13
<211> LENGTH: 52
<212> TYPE: DNA
<213> ORGANISM: Artificial Sequence
<220> FEATURE:
<223> OTHER INFORMATION: pLFYGW-FW primer

<400> SEQUENCE: 13
ggggacaagt ttgtacaaaa aagcaggcta cggatccatt tttcgcaaag ga                52

<210> SEQ ID NO 14
<211> LENGTH: 49
<212> TYPE: DNA
<213> ORGANISM: Artificial Sequence
<220> FEATURE:
<223> OTHER INFORMATION: RGL1/rgl1GW-RV primer

<400> SEQUENCE: 14
ggggacaagt ttgtacaaaa aagcaggcta tgaagagaga gcacaacca                    49

<210> SEQ ID NO 15
<211> LENGTH: 19
<212> TYPE: DNA
<213> ORGANISM: Artificial Sequence
<220> FEATURE:
<223> OTHER INFORMATION: ela1-1-LP primer

<400> SEQUENCE: 15
atggagaatt ttatggtag                                                     19

<210> SEQ ID NO 16
<211> LENGTH: 21
<212> TYPE: DNA
<213> ORGANISM: Artificial Sequence
<220> FEATURE:
<223> OTHER INFORMATION: ela1-1-RP primer

<400> SEQUENCE: 16
atctcccaca cattcccttt c                                                  21

<210> SEQ ID NO 17
<211> LENGTH: 21
<212> TYPE: DNA
<213> ORGANISM: Artificial Sequence
```

```
<220> FEATURE:
<223> OTHER INFORMATION: ela1-2-LP primer

<400> SEQUENCE: 17
tggcgaaaac aatacggtaa g                                              21

<210> SEQ ID NO 18
<211> LENGTH: 21
<212> TYPE: DNA
<213> ORGANISM: Artificial Sequence
<220> FEATURE:
<223> OTHER INFORMATION: ela1-2-RP

<400> SEQUENCE: 18
tgatggcctt ttgaagacat c                                              21

<210> SEQ ID NO 19
<211> LENGTH: 19
<212> TYPE: DNA
<213> ORGANISM: Artificial Sequence
<220> FEATURE:
<223> OTHER INFORMATION: ela1-3-LP primer

<400> SEQUENCE: 19
atggagaatt ttatggtag                                                 19

<210> SEQ ID NO 20
<211> LENGTH: 21
<212> TYPE: DNA
<213> ORGANISM: Artificial Sequence
<220> FEATURE:
<223> OTHER INFORMATION: ela1-3-RP primer

<400> SEQUENCE: 20
atctcccaca cattcccttt c                                              21

<210> SEQ ID NO 21
<211> LENGTH: 19
<212> TYPE: DNA
<213> ORGANISM: Artificial Sequence
<220> FEATURE:
<223> OTHER INFORMATION: LBb1.3 primer

<400> SEQUENCE: 21
attttgccga tttcggaac                                                 19

<210> SEQ ID NO 22
<211> LENGTH: 23
<212> TYPE: DNA
<213> ORGANISM: Artificial Sequence
<220> FEATURE:
<223> OTHER INFORMATION: pSKTAIL-L3 primer

<400> SEQUENCE: 22
atacgacgga tcgtaatttg tcg                                            23

<210> SEQ ID NO 23
<211> LENGTH: 30
<212> TYPE: DNA
<213> ORGANISM: Artificial Sequence
<220> FEATURE:
<223> OTHER INFORMATION: pELALFYm1,2 primer

<400> SEQUENCE: 23
aataagaggg accaagcttt agaaaaagag                                     30
```

<210> SEQ ID NO 24
<211> LENGTH: 52
<212> TYPE: DNA
<213> ORGANISM: Artificial Sequence
<220> FEATURE:
<223> OTHER INFORMATION: pELALFYm3,4 primer

<400> SEQUENCE: 24
gtgtatggaa agcttgacaa attaaatgta taggtagaaa gcttggctac ag    52

<210> SEQ ID NO 25
<211> LENGTH: 20
<212> TYPE: DNA
<213> ORGANISM: Artificial Sequence
<220> FEATURE:
<223> OTHER INFORMATION: ELA1-FW primer

<400> SEQUENCE: 25
tggtagagat ggccaagacc    20

<210> SEQ ID NO 26
<211> LENGTH: 20
<212> TYPE: DNA
<213> ORGANISM: Artificial Sequence
<220> FEATURE:
<223> OTHER INFORMATION: ELA1-RV primer

<400> SEQUENCE: 26
ggacgaatga ctgagggtgt    20

<210> SEQ ID NO 27
<211> LENGTH: 20
<212> TYPE: DNA
<213> ORGANISM: Artificial Sequence
<220> FEATURE:
<223> OTHER INFORMATION: ELA1-FW primer

<400> SEQUENCE: 27
tccgcgatga agtctttctt    20

<210> SEQ ID NO 28
<211> LENGTH: 20
<212> TYPE: DNA
<213> ORGANISM: Artificial Sequence
<220> FEATURE:
<223> OTHER INFORMATION: ELA1-RV primer

<400> SEQUENCE: 28
ttgtgtcctc aagggcttct    20

<210> SEQ ID NO 29
<211> LENGTH: 20
<212> TYPE: DNA
<213> ORGANISM: Artificial Sequence
<220> FEATURE:
<223> OTHER INFORMATION: ELA1(upstream)-FW primer

<400> SEQUENCE: 29
tggtagagat ggccaagacc    20

<210> SEQ ID NO 30
<211> LENGTH: 20
<212> TYPE: DNA
<213> ORGANISM: Artificial Sequence
<220> FEATURE:
<223> OTHER INFORMATION: ELA1(upstream)-RV

```
<400> SEQUENCE: 30
attgctccgc catcacttta                                              20

<210> SEQ ID NO 31
<211> LENGTH: 20
<212> TYPE: DNA
<213> ORGANISM: Artificial Sequence
<220> FEATURE:
<223> OTHER INFORMATION: ELA1(flanking)-FW

<400> SEQUENCE: 31
gcgaaaacaa tacgggagag                                              20

<210> SEQ ID NO 32
<211> LENGTH: 19
<212> TYPE: DNA
<213> ORGANISM: Artificial Sequence
<220> FEATURE:
<223> OTHER INFORMATION: ELA1(flanking)-RV

<400> SEQUENCE: 32
aactccgggt ggttcatgt                                               19

<210> SEQ ID NO 33
<211> LENGTH: 20
<212> TYPE: DNA
<213> ORGANISM: Artificial Sequence
<220> FEATURE:
<223> OTHER INFORMATION: GA20ox2-FW

<400> SEQUENCE: 33
ctccggcaga gaaagaacac                                              20

<210> SEQ ID NO 34
<211> LENGTH: 20
<212> TYPE: DNA
<213> ORGANISM: Artificial Sequence
<220> FEATURE:
<223> OTHER INFORMATION: GA20ox2-RV

<400> SEQUENCE: 34
cccaattcga aaaggaatcg                                              20

<210> SEQ ID NO 35
<211> LENGTH: 20
<212> TYPE: DNA
<213> ORGANISM: Artificial Sequence
<220> FEATURE:
<223> OTHER INFORMATION: AP1-FW

<400> SEQUENCE: 35
gaaggccata caggagcaaa                                              20

<210> SEQ ID NO 36
<211> LENGTH: 20
<212> TYPE: DNA
<213> ORGANISM: Artificial Sequence
<220> FEATURE:
<223> OTHER INFORMATION: AP1-RV

<400> SEQUENCE: 36
actgctcctg ttgagcccta                                              20

<210> SEQ ID NO 37
```

-continued

<210> SEQ ID NO 37
<211> LENGTH: 23
<212> TYPE: DNA
<213> ORGANISM: Artificial Sequence
<220> FEATURE:
<223> OTHER INFORMATION: TUB2-FW

<400> SEQUENCE: 37
agcaatacca agatgcaact gcg                                           23

<210> SEQ ID NO 38
<211> LENGTH: 27
<212> TYPE: DNA
<213> ORGANISM: Artificial Sequence
<220> FEATURE:
<223> OTHER INFORMATION: TUB2-RV

<400> SEQUENCE: 38
taactaaatt attctcagta ctcttcc                                       27

<210> SEQ ID NO 39
<211> LENGTH: 26
<212> TYPE: DNA
<213> ORGANISM: Artificial Sequence
<220> FEATURE:
<223> OTHER INFORMATION: EIF4-FW

<400> SEQUENCE: 39
aaactcaatg aagtacttga gggaca                                        26

<210> SEQ ID NO 40
<211> LENGTH: 26
<212> TYPE: DNA
<213> ORGANISM: Artificial Sequence
<220> FEATURE:
<223> OTHER INFORMATION: EIF4-RV primer

<400> SEQUENCE: 40
tctcaaaacc ataagcataa ataccc                                        26

<210> SEQ ID NO 41
<211> LENGTH: 34
<212> TYPE: DNA
<213> ORGANISM: Artificial Sequence
<220> FEATURE:
<223> OTHER INFORMATION: pAP1-FW primer

<400> SEQUENCE: 41
ttcagtgagc tcgggttctc accttattcc aaaa                               34

<210> SEQ ID NO 42
<211> LENGTH: 32
<212> TYPE: DNA
<213> ORGANISM: Artificial Sequence
<220> FEATURE:
<223> OTHER INFORMATION: pAP1-RV primer

<400> SEQUENCE: 42
catcgactcg agaggatttg cgtgtcgact tc                                 32

<210> SEQ ID NO 43
<211> LENGTH: 51
<212> TYPE: DNA
<213> ORGANISM: Artificial Sequence
<220> FEATURE:
<223> OTHER INFORMATION: SPL9-FW primer

<400> SEQUENCE: 43

```
gggggacaagt ttgtacaaaa aagcaggcta catggagatg ggttccaact c        51
```

<210> SEQ ID NO 44
<211> LENGTH: 50
<212> TYPE: DNA
<213> ORGANISM: Artificial Sequence
<220> FEATURE:
<223> OTHER INFORMATION: SPL9-RV primer

<400> SEQUENCE: 44

```
ggggaccact ttgtacaaga aagctgggtt tcagagagac cagttggtat           50
```

<210> SEQ ID NO 45
<211> LENGTH: 49
<212> TYPE: DNA
<213> ORGANISM: Artificial Sequence
<220> FEATURE:
<223> OTHER INFORMATION: RGA-FW primer

<400> SEQUENCE: 45

```
ggggacaagt ttgtacaaaa aagcaggcta tgaagagaga tcatcacca            49
```

<210> SEQ ID NO 46
<211> LENGTH: 49
<212> TYPE: DNA
<213> ORGANISM: Artificial Sequence
<220> FEATURE:
<223> OTHER INFORMATION: RGA-RV primer

<400> SEQUENCE: 46

```
ggggaccact ttgtacaaga aagctgggtt cagtacgccg ccgtcgaga            49
```

<210> SEQ ID NO 47
<211> LENGTH: 20
<212> TYPE: DNA
<213> ORGANISM: Artificial Sequence
<220> FEATURE:
<223> OTHER INFORMATION: AP1-a-F primer

<400> SEQUENCE: 47

```
tcgaacgtgg tggttagaag                                            20
```

<210> SEQ ID NO 48
<211> LENGTH: 21
<212> TYPE: DNA
<213> ORGANISM: Artificial Sequence
<220> FEATURE:
<223> OTHER INFORMATION: AP1-a-R primer

<400> SEQUENCE: 48

```
cgcagcagct agcatctatt t                                          21
```

<210> SEQ ID NO 49
<211> LENGTH: 21
<212> TYPE: DNA
<213> ORGANISM: Artificial Sequence
<220> FEATURE:
<223> OTHER INFORMATION: AP1-b-F primer

<400> SEQUENCE: 49

```
caaaccttcc tgccttcttt t                                          21
```

<210> SEQ ID NO 50
<211> LENGTH: 25
<212> TYPE: DNA

<213> ORGANISM: Artificial Sequence
<220> FEATURE:
<223> OTHER INFORMATION: AP1-b-R primer

<400> SEQUENCE: 50
aatatctcga tccactaaga tacgg                                    25

<210> SEQ ID NO 51
<211> LENGTH: 20
<212> TYPE: DNA
<213> ORGANISM: Artificial Sequence
<220> FEATURE:
<223> OTHER INFORMATION: AP1-c-F primer

<400> SEQUENCE: 51
gcaaatgccg aatctgtttt                                          20

<210> SEQ ID NO 52
<211> LENGTH: 21
<212> TYPE: DNA
<213> ORGANISM: Artificial Sequence
<220> FEATURE:
<223> OTHER INFORMATION: AP1-c-R primer

<400> SEQUENCE: 52
aaaaaccttt gctcaatttg c                                        21

<210> SEQ ID NO 53
<211> LENGTH: 20
<212> TYPE: DNA
<213> ORGANISM: Artificial Sequence
<220> FEATURE:
<223> OTHER INFORMATION: AP1-d-F primer

<400> SEQUENCE: 53
acacttgggg aaggaccagt                                          20

<210> SEQ ID NO 54
<211> LENGTH: 20
<212> TYPE: DNA
<213> ORGANISM: Artificial Sequence
<220> FEATURE:
<223> OTHER INFORMATION: AP1-d-R primer

<400> SEQUENCE: 54
atgtcgggtc catgattttt                                          20

<210> SEQ ID NO 55
<211> LENGTH: 24
<212> TYPE: DNA
<213> ORGANISM: Artificial Sequence
<220> FEATURE:
<223> OTHER INFORMATION: AP1-e-F primer

<400> SEQUENCE: 55
aatgtgtcgc atctaagaag attt                                     24

<210> SEQ ID NO 56
<211> LENGTH: 21
<212> TYPE: DNA
<213> ORGANISM: Artificial Sequence
<220> FEATURE:
<223> OTHER INFORMATION: AP1-e-R primer

<400> SEQUENCE: 56
tcgagttcta actgcggttt c                                        21

```
<210> SEQ ID NO 57
<211> LENGTH: 22
<212> TYPE: DNA
<213> ORGANISM: Artificial Sequence
<220> FEATURE:
<223> OTHER INFORMATION: pELA1(transgene)-F primer

<400> SEQUENCE: 57
tgtttggtca aaaggatagt gc                                              22

<210> SEQ ID NO 58
<211> LENGTH: 20
<212> TYPE: DNA
<213> ORGANISM: Artificial Sequence
<220> FEATURE:
<223> OTHER INFORMATION: pELA1(transgene)-R primer

<400> SEQUENCE: 58
gcgggatatc accactttgt                                                 20

<210> SEQ ID NO 59
<211> LENGTH: 21
<212> TYPE: DNA
<213> ORGANISM: Artificial Sequence
<220> FEATURE:
<223> OTHER INFORMATION: EIF4-FW primer

<400> SEQUENCE: 59
tgttttgctt cgtttcaagg a                                               21

<210> SEQ ID NO 60
<211> LENGTH: 19
<212> TYPE: DNA
<213> ORGANISM: Artificial Sequence
<220> FEATURE:
<223> OTHER INFORMATION: EIF4-RV primer

<400> SEQUENCE: 60
gcattttccc gattacaac                                                  19
```

COMPOSITIONS AND METHODS FOR CONTROLLING PLANT GROWTH AND DEVELOPMENT

CROSS-REFERENCE TO RELATED APPLICATIONS

This application is a National Phase Application of PCT International Application No. PCT/US2015/027993, International Filing Date Apr. 28, 2015, claiming priority of Provisional Patent Application(s) No. 61/985,315, filed Apr. 28, 2014, which are hereby incorporated by reference.

STATEMENT RECORDING FEDERALLY SPONSORED RESEARCH OR DEVELOPMENT

This invention was made with government support under Grant Numbers IOS 0849298 and 1257111 awarded by the National Science Foundation. The government has certain rights in the invention.

FIELD OF THE INVENTION

The invention relates generally to molecules for controlling plant growth and development. Specifically, the invention relates to molecules comprising a 'gibberellin activator' or 'gibberellin inhibitor' operably linked to a promoter specific to a lateral organ primordium. The invention also relates to transgenic plants having the transgenic molecules and methods for making such transgenic plants.

BACKGROUND OF THE INVENTION

Synchronization of the developmental transitions that lead to reproductive competence is important for species survival. Plants form new lateral organs iteratively throughout their life from the flanks of the shoot apical meristem. The type of the lateral organ produced depends on the phase of the lifecycle. In *Arabidopsis*, rosette leaves are produced during the vegetative phase. During the reproductive phase, an inflorescence forms. Not all lateral organ primordia of the inflorescence are competent to become flowers. The biphasic transition to reproduction thus involves two events: first, the switch from vegetative development to the inflorescence and second, flower formation. The duration of the pre-floral inflorescence phase is critical for optimal seed set.

Accordingly, a need exists to understand the mechanisms of the regulation of the transition from inflorescence to floral fate, and thereby improve reproductive success and crop yield.

SUMMARY OF THE INVENTION

In one aspect, the invention relates to a recombinant nucleic acid molecule comprising: a transgenic nucleic acid sequence comprising a sequence encoding a floral fate inducer operably linked to a promoter specific to flower primordium or lateral organ primordium, wherein said floral fate inducer is associated with gibberellin biosynthesis. In an exemplary embodiment, the floral fate inducer is a gibberellin inhibitor.

In another aspect, the invention relates to a recombinant nucleic acid molecule comprising: a first transgenic sequence and a second transgenic sequence, said first transgenic sequence comprising a nucleic acid sequence encoding a gibberellin activator operably linked to a vegetative stage specific promoter or lateral organ specific promoter and a second transgenic sequence comprising a nucleic acid sequence encoding a gibberellin inhibitor operably linked to a flower primordium specific promoter or a lateral organ primordium specific promoter.

In another aspect, the invention relates to a method for generating a transgenic plant, the method comprising: transforming a cell of the plant substantially the same genetic background with a nucleic acid molecule to obtain a recombinant plant cell; and generating a transgenic plant from said recombinant plant cell, wherein said nucleic acid molecule is the molecule of the invention. In some embodiments, the method further comprises the steps of: determining whether the transgenic molecule is stably integrated into the genome of said plant; and determining whether the transgenic molecule is effective in inducing floral fate or its associated phenotypic trait in said transgenic plant. In a particular embodiment, the invention includes the step of growing said plant to obtain a seed, thereby producing said seed of said plant.

In another aspect, the invention relates to a method for inducing a floral fate to improve reproductive development in a plant, the method comprising: applying a gibberellin inhibitor during the flower primordium developmental stage or after the termination of vegetative stage of said plant.

In another aspect, the invention relates to a method for improving yield in a crop plant, the method comprising: applying a gibberellin or its activator during a vegetative stage of said crop plant; and applying a gibberellin inhibitor after the termination of vegetative stage of said plant.

In another aspect, the invention relates to a formulation for a plant growth, said formulation comprising a first composition and a second composition, said first composition comprising a gibberellin or its activator in combination with a fast release polymer component, wherein said first composition is capable of releasing said gibberellin or its activator soon after its application to a plant in vegetative stage; and said second composition comprising a gibberellin inhibitor in combination with a slow release or a delayed release polymer component, wherein said second composition is capable of releasing said gibberellin or its activator later during a lateral organ primordium or a flower primordium developmental stage.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

FIG. 4. Gibberellin-sensitive DELLA transcriptional co-regulators promote floral fate. (A) qRT-PCR determination of AP1 induction relative to mock treated plants. Treatments: dexamethasone (Dex), gibberellin biosynthesis inhibitor paclobutrazol (PAC). (B) Anti-HA and Anti-FLAG ChIP-qPCR of pRGA:RGA-HA and pSPL9:rSPL9-FLAG inflorescences. WT: ChIP in nontransgenic wild-type plants. NC: negative control locus. Below: AP1 promoter with PCR fragments amplified. Asterisks: SPL binding motifs, triangles: LFY binding motifs. (C) qRT-PCR determination of AP1 induction relative to mock treated plants. Treatments: Dex, PAC, ethanol vapor induction of ETOH:miR156f to deplete miR156-sensitive SPL proteins, or gibberellin (GA) to deplete DELLA proteins. (D) pRGA:RGA-HA association with the AP1 locus "d" region in the presence (−ETOH) or absence (+ETOH) of miR156-sensitive SPL proteins. ChIP controls were as in (B). (A-D) Mean±SEM. (E) Immediate switch to flower formation in plants with increased LFY (35S:LFY), SPL9 (mir156 resistant pSPL9:rSPL9-FLAG) and DELLA (PAC treatment) levels. The number of cauline leaves formed in 35S:LFY pSPL9:rSPL9-FLAG PAC plants (0.3±0.1) was significantly lower ($P<10^{-16}$, two-sided Student's t-test) than that of 35S:LFY plants (2.5±0.2). (F) LFY and SPL9/DELLA synergistically induce AP1.

(mutated). (C) Left: Qualitatively similar spatial expression of gELA1-GFP and pELA1:GFP-GUS based on confocal imaging of live inflorescences. Right: pELA1:GFP-GUS expression was undetectable in lfy null mutant floral primordia. (D) Mutation of the LFY binding sites in pELA1m:GFP-GUS strongly reduced LFY association with the ELA1 promoter based on ChIP-qPCR. Control ChIP-qPCR reaction was performed on pELA1:GFP-GUS. NC: negative control locus (promoter of EIF4A (At3g13920)). Scale bar: 50 µm.

Figure 9:
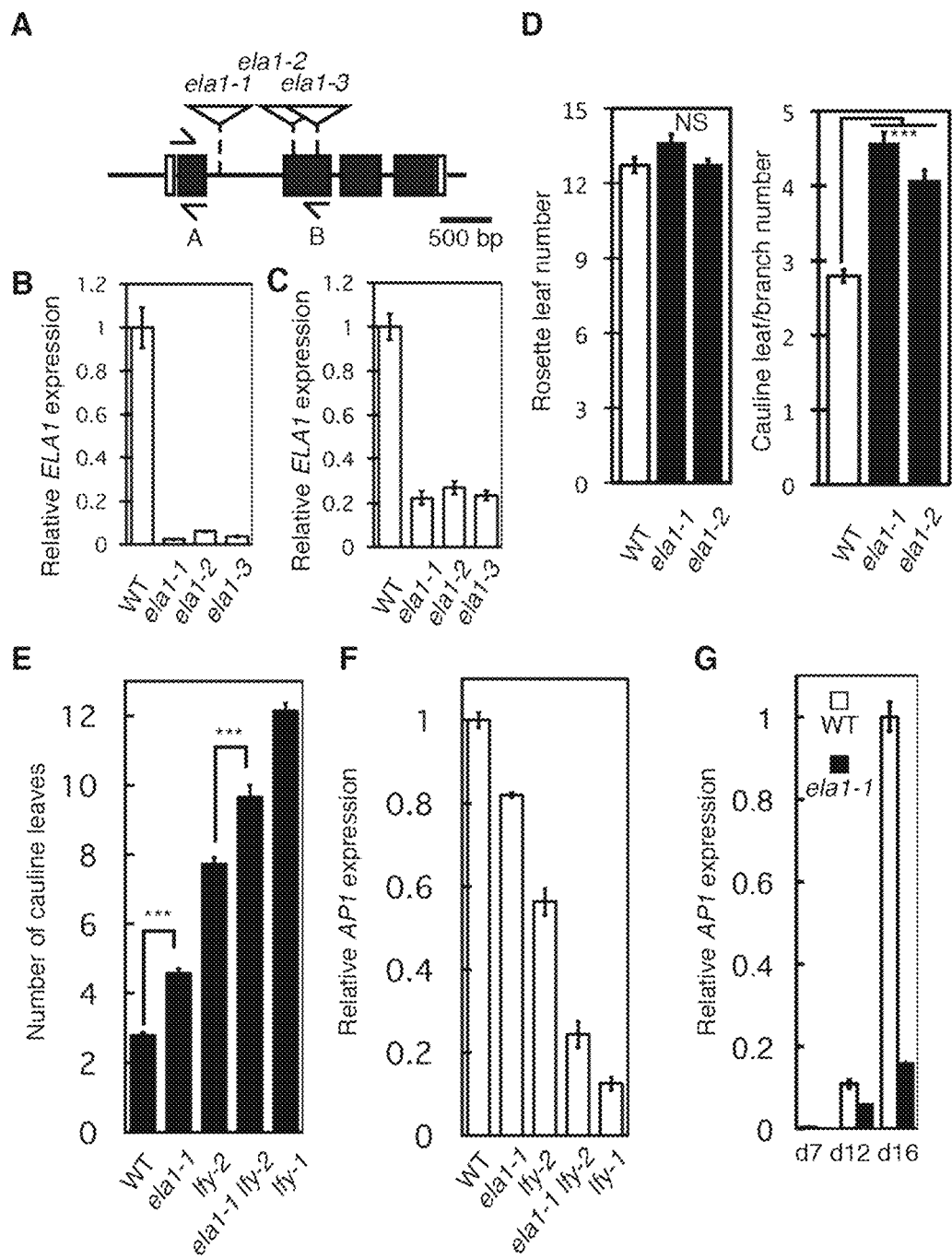

FIG. 9. ELA1 mutant alleles and effect of ELA1 loss-of-function on the timing of the formation of the first flower. (A) Diagram of the ELA1 locus. Black line: intergenic region and introns. White box: 5'UTR. Grey box: 3'UTR. Black boxes: exons. The location of three T-DNA insertions (SALK_005782, SALK_049907, and SK6964) is indicated. Arrow above: forward primer. Arrows below: reverse primers. (B, C) qRT-PCR using the forward primer and reverse primer A (B) and B (C) to test for a reduction in the steady state ELA1 mRNA level. (D) Effect of loss-of ELA1 function on developmental transitions. Consistent with the very low expression of ELA1 during vegetative development (FIG. 7), ela1 mutants did not delay the switch from vegetative development to formation of the inflorescence. No significant increase in the number of rosette leaves was observed compared to the wild type (WT). However, ela1 mutants did delay the switch to flower formation (longer first inflorescence phase). This is evidenced by a significant increase in the number of cauline leaves (and branches) relative to the wild type. NS (not significant) P=0.07 ela1-1, P=0.93 ela1-2, for rosette leaf number; *P<$10^{-4}$ for cauline leaf and branch number; two-sided Student's t-test. (E) The ela1-1 mutant also significantly delayed flower formation in the hypomorph lfy-2 mutant background. lfy-1 is a null mutant (31).*P<$10^{-5}$, for cauline leaf and branch number, two-sided Student's t-test. (F) Relative expression of the floral commitment factor AP1 in the plants shown in (E). AP1 expression in the wild type (WT) was set to 1. (G) Relative expression of AP1 in the wild type and ela1-1 at different stages of development (the vegetative phase (day 7), the first inflorescence phase (day 12), and the second inflorescence phase (day 16)). AP1 expression in the wild type (WT) at day 16 was set to 1.

Figure 10:
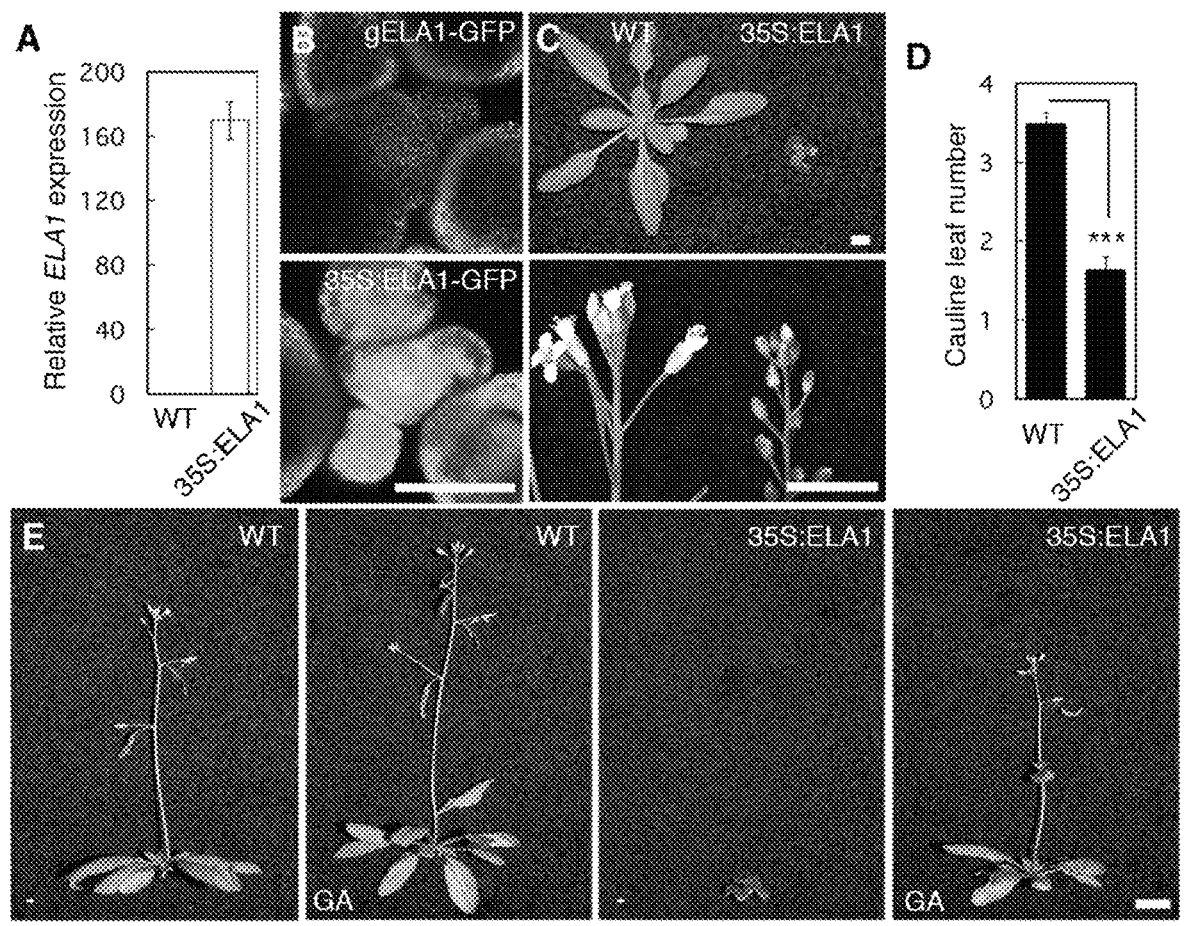

FIG. 10. Phenotype of ELA1 overexpressing plants. (A, B) ELA1-GFP RNA and protein levels when overexpressed from the constitutive cauliflower mosaic virus 35S promoter as determined by qRT-PCR (A) or confocal imaging (B). gELA1-GFP expression is shown as a control. Pictures were taken using the same settings. Scale bar: 50 µm. (C) Vegetative (top) and reproductive (bottom) phenotypes of 35S:ELA1-GFP plants. Relative to the wild type, ELA1-GFP overexpressing plants were dwarfed with small dark green leaves and short internodes and pedicels. The observed phenotypes are similar to those previously reported for 35S:ELA1. Bars: 1 cm (top), 5 mm (bottom). (D) 35S:ELA1-GFP plants displayed a shorter first inflorescence phase, significantly (***P<$10^{-6}$, two-sided Student's t-test) fewer cauline leaves formed prior flower formation. (E) Effect of gibberellin treatment on wild-type and 35S:ELA1 plants. The extreme dwarf phenotype of 35S:ELA1 was partly rescued by treatment with exogenous gibberellin (100 µM).

Figure 11:
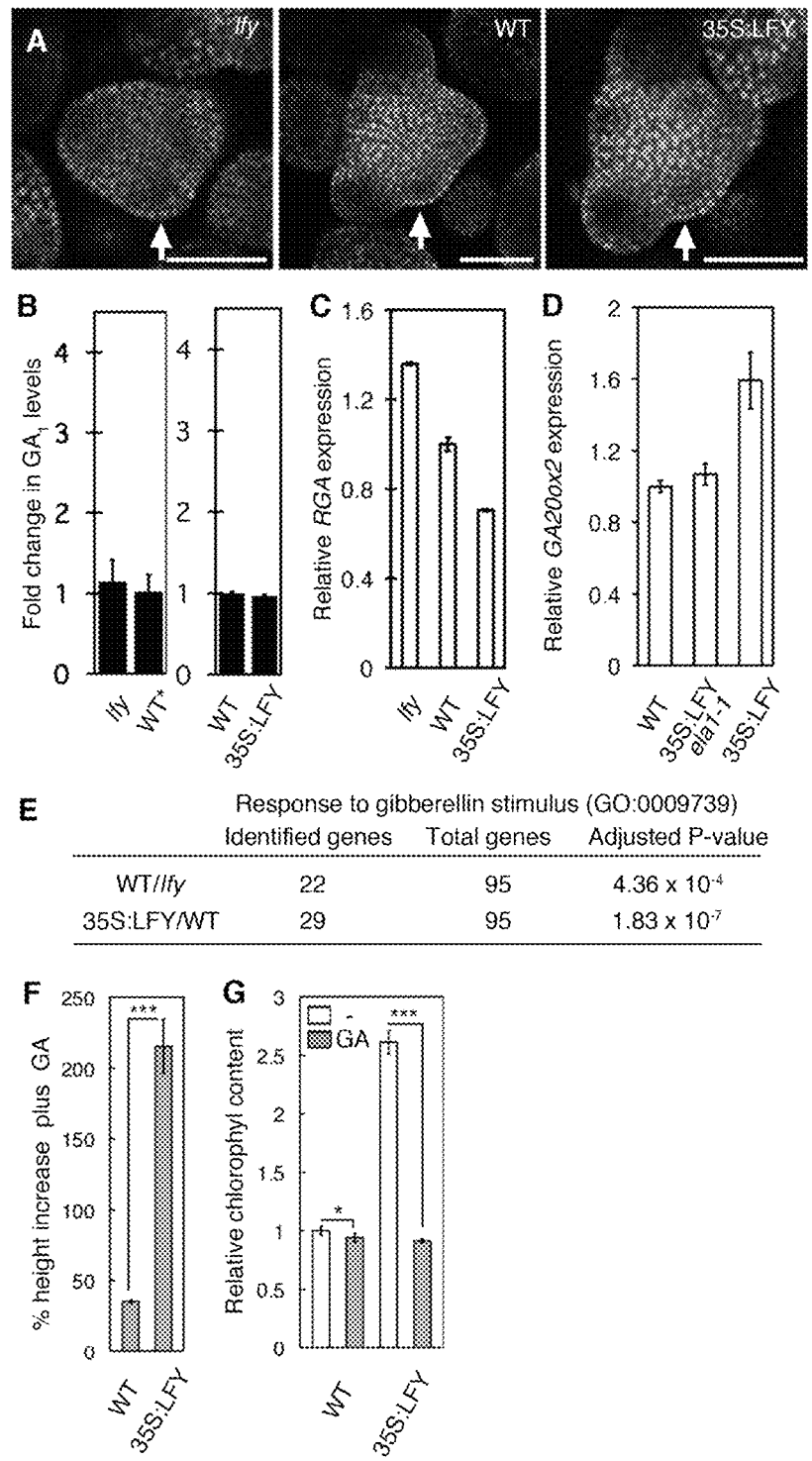

FIG. 11. Link between LFY and the gibberellin pathway in inflorescences. (A) DELLA protein (RGA-GFP) expression in different genetic backgrounds. DELLA proteins are degraded upon gibberellin sensing. Confocal images to visualize the expression domain and signal intensity for pRGA:RGA-GFP in lfy null mutant (left), wild type (WT, center) and LFY overexpressing (35S:LFY, right) inflorescences. Arrows point to newly formed flower primordia. Scale bar: 50 µm. (B) Plants with altered LFY activity do not have altered $GA_1$ levels. Although we observed significant changes in $GA_4$ levels in plants with reduced or increased LFY activity (FIG. 2A), there was no significant effect on $GA_1$ levels (P=0.69 lfy versus control inflorescences, P=0.46 35S:LFY versus control, two-sided Student's t-test). This is consistent with the published activity of ELA1 in the $GA_4$-producing branch of the pathway. (C) RGA mRNA accumulation in lfy mutant, wild-type and 35S:LFY inflorescences. RGA mRNA levels—unlike RGA protein levels (FIG. 2B)—are positively correlated with gibberellin accumulation, as previously reported. (D) GA20ox2 expression levels. The increased GA20ox2 expression observed in 35S:LFY plants (FIG. 2C) was reduced to wild-type levels in 35S:LFY ela1-1 plants. (E) Gene ontology (GO) term enrichment analysis. The GO term "response to gibberellin stimulus" was enriched among genes significantly (FDR<0.01) differentially expressed in lfy mutant relative to the wild-type inflorescences (1993 genes, 21-day-old inflorescences). The GO term "response to gibberellin stimulus" was enriched among genes significantly (FDR<0.01) differentially expressed in LFY overexpressing plants relative to wild type (1804 genes, dexamethasone treatment of 35S:LFY-GR and wild-type plants). To identify enriched GO terms we employed ChipEnrich with recent GO annotations downloaded from TAIR (3/5/13No.). We performed an FDR correction in R using the Benjami-Hochberg method to obtain adjusted p-values. (F, G) Partial rescue of 35S:LFY phenotypic defects after gibberellin application. (F) Strongly increased plant height of 35S:LFY plants after application of gibberellin (100 µM). Shown is the percent increase relative to mock treated plants of the same genotype. Error bars: mean+/−SEM. P-value ***<$10^{-4}$, two-sided Students t-test. (G) Chlorophyll content in 1 cm diameter leaf discs isolated from wild type (WT) or 35S:LFY plants. Plants were mock treated or treated with 100 µM GA. The chlorophyll content was normalized by the average obtained for mock treated wild type plants. Mean+/−SEM are shown. P-values *<0.01, ***<$10^{-6}$ two-sided Students t-test.

Figure 3:
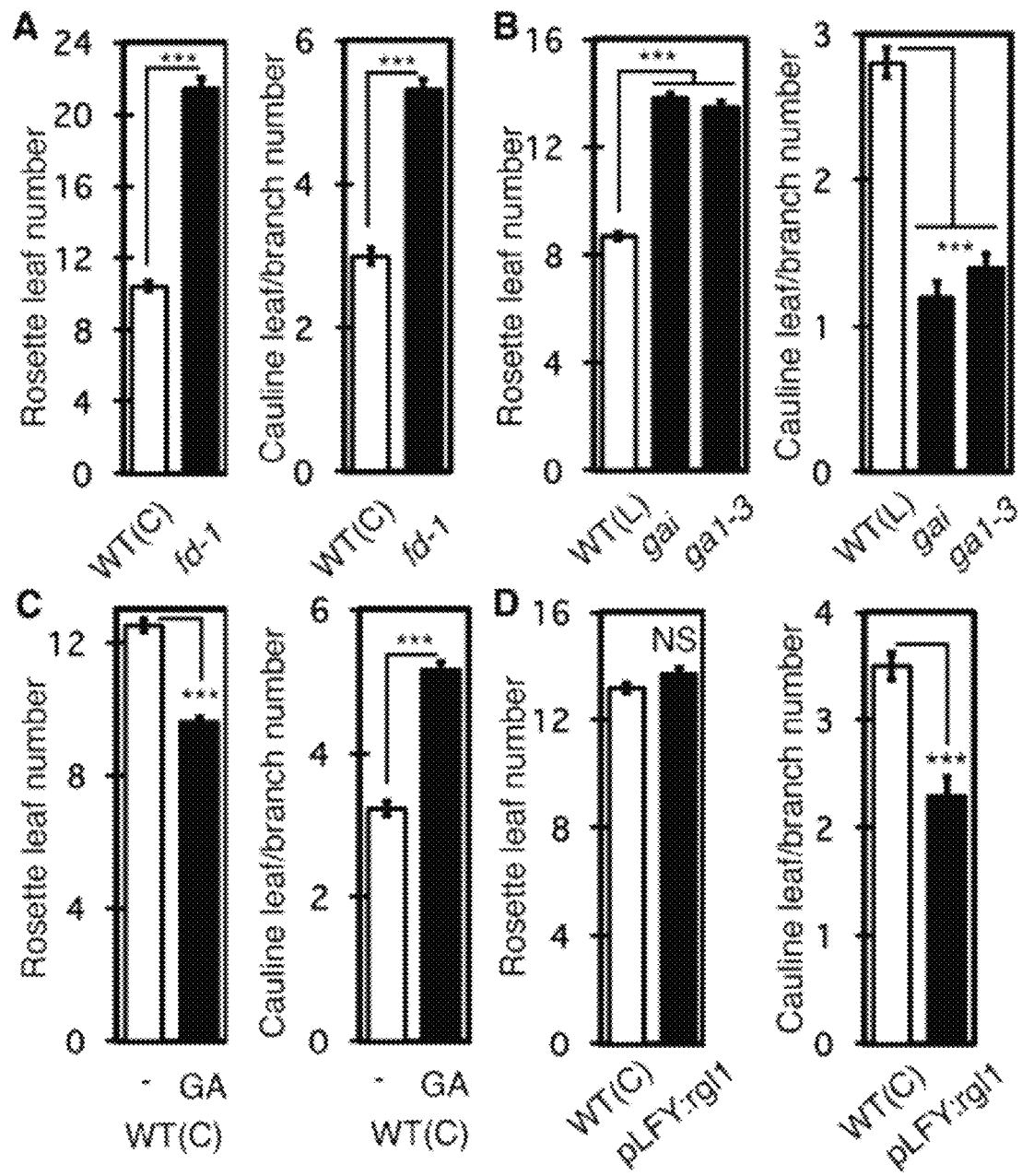
FIG. 3. Gibberellin inhibits the switch to flower formation. (A-D) Duration of the vegetative phase (number of rosette leaves formed) and of the first inflorescence phase (number of cauline leaves and associated branches formed) in long-day photoperiods. White bar (control) and black bar (experimental) genotype or treatment. Mean±SEM are shown. Asterisks (***) $P<10^{-6}$ based on two-sided Student's t-test. NS: not significant (P=0.25 two-sided Student's t-test) (A) Typical effect of a mutant (fd-1 (20)) that prolongs both phases. (B) Mutants with decreased gibberellin (GA) response (gai) or levels (gal-3). (C) Treatment with exogenous GA. (D) Reduction of the GA response specifically in incipient flower primordia (pLFY:rgl1). Throughout, matched WT genotypes were employed (WT (L): wild type in the Ler accession, WT (C): wild type in the Columbia accession).
Figure 5:
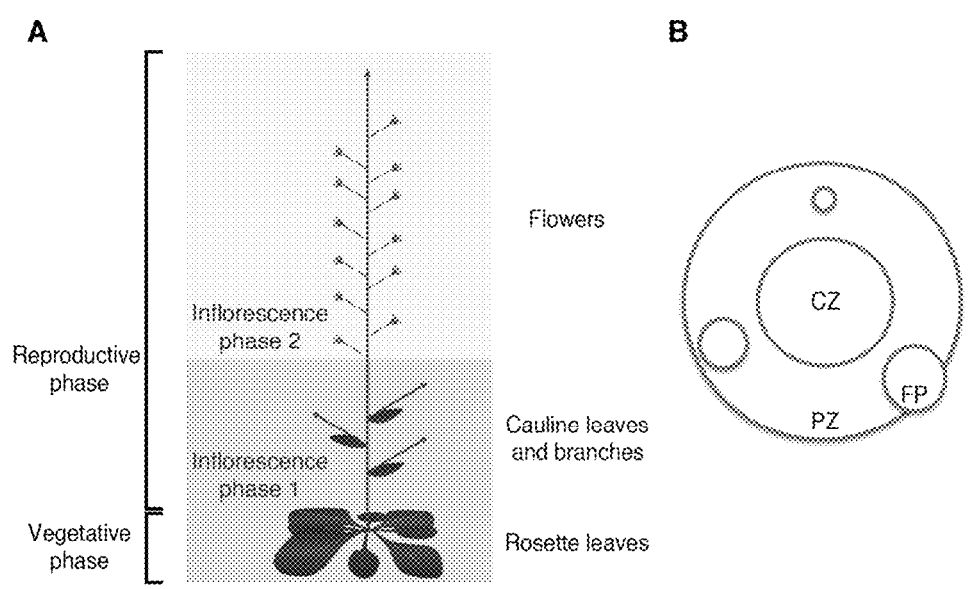
FIG. 5. *Arabidopsis* inflorescence architecture. (A) Diagram of an adult *Arabidopsis* plant. Different lateral organs are formed during each phase of the plant life cycle. During the vegetative phase, lateral primordia give rise to rosette leaves. Subsequently, during the reproductive phase, an inflorescence forms. Not all lateral primordia on the inflorescence are competent to adopt a floral fate, some give rise to cauline leaves with associated branches during the first inflorescence phase. During second inflorescence phase, flowers form. (B) Top view of the inflorescence apex with the stem cell pool containing central zone (CZ) and the peripheral zone (PZ) from where flower primordia (small circles, FP) arise.
Figure 12:
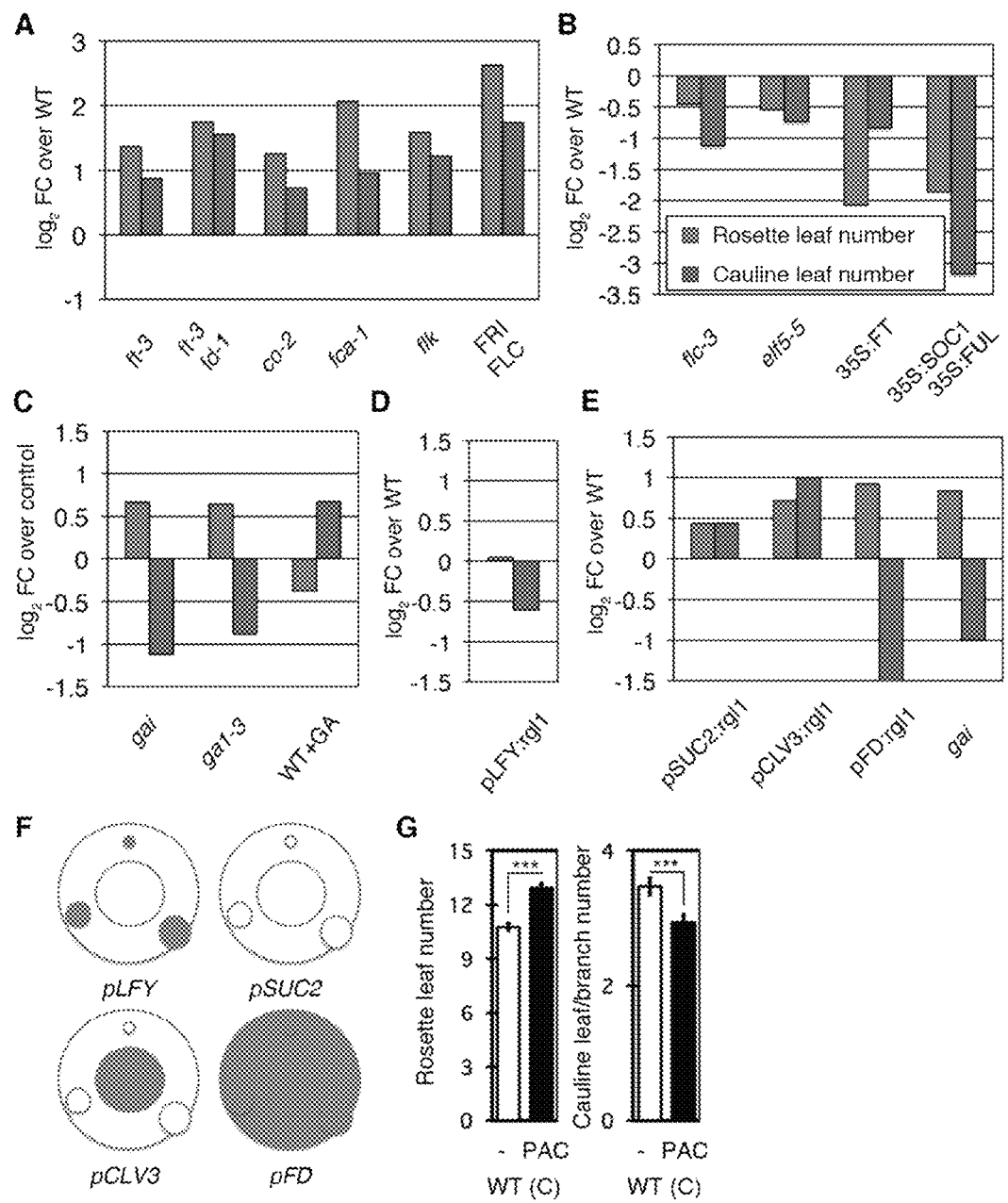

FIG. 12. Duration of rosette-leaf producing vegetative and cauline-leaf and branch producing first inflorescence phase in various genetic backgrounds. (A, B) Analysis of published mutants, which delay or accelerate the switch to reproductive development. Data sources are: ft-3, ft-3 fd-1, co-2, 35S:FT, 35S:SOC1 35S:FUL, fca-1, flk, FRI FLC, flc-3, elf-5. The $\log_2$ fold change in the number of rosette or cauline leaves produced relative to wild-type plants is plotted. All mutants cause a coordinate change in the number of rosette leaves (longer vegetative phase) and in the number of cauline leaves formed (longer first inflorescence phase) formed. (C) $\log_2$ fold change of the number of rosette or cauline leaves produced by plants shown in FIG. 3. gai: gibberellin (GA) insensitive mutant, ga1-3: gibberellin biosynthesis mutant, gibberellin (100 µM) versus mock treated wild type plants. Reduction or increase in gibberellin levels/response had opposite effects on the number of rosette leaves (length of vegetative phase) and cauline leaves formed (length of first inflorescence phase). (D) Reducing gibberellin response or levels in a spatially restricted manner (in incipient flower primordia) by expressing the stabilized DELLA protein rgl1 from the LFY promoter decreased the number of cauline leaves formed but had no effect on the number of rosette leaves formed (see also FIG. 3D). (E) Published data for misexpression of a stabilized DELLA protein (rgl1) in tissues that do not include (pCLV3, pSUC2) or do include (pFD) the peripheral zone of the shoot apex, where flower primordia initiate. A reduction of gibberellin response in plant tissues that exclude the peripheral zone of the shoot apex caused a coordinate increase in the number of rosette and cauline leaves formed, as do the mutants shown in (A, B). By contrast, a reduction of gibberellin response in plant tissues that include the peripheral region of the shoot apex caused an increase in the number of rosette leaves and a reduction in the number of cauline leaves formed. Published data for the gai mutant is included for comparison. (F) Reduced gibberellin response in the peripheral zone of the inflorescence apex and in incipient flower primordia promotes flower formation. Diagram of the shoot apex indicating the domains of rgl1 was misexpression in (D, E). From left to right: pLFY (expressed in flower primordia), pSUC2 (not expressed in the shoot apex), pCLV3 (expressed in the central zone), pFD (expressed in the central and peripheral zone). (G) Duration of the vegetative phase and of the first inflorescence phase in plants treated with the gibberellin biosynthesis inhibitor paclobutrazol (1 µM).

Figure 13:
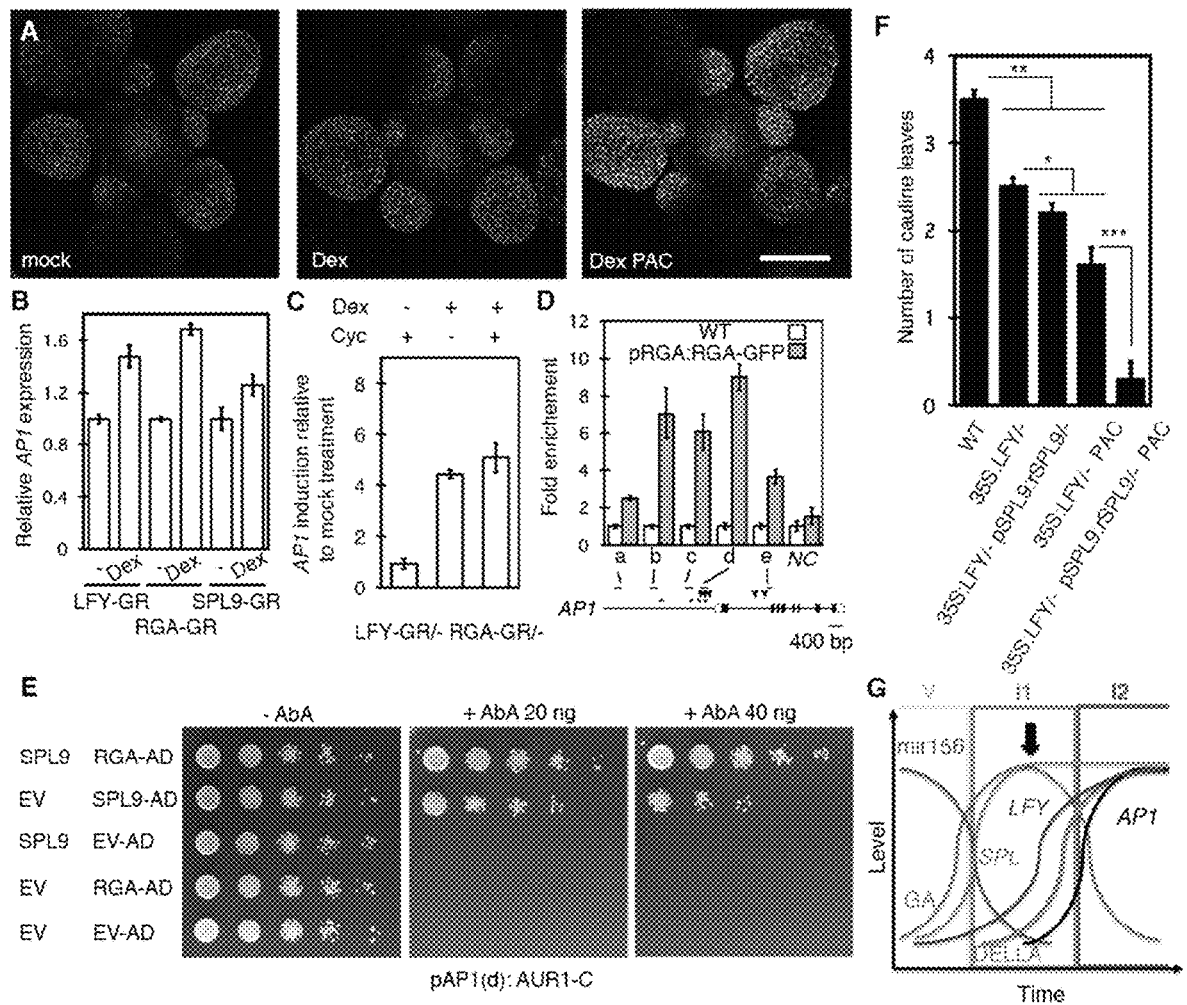

FIG. 13. The role of LFY, SPL9 and RGA/DELLA in AP1 induction and in formation of the first flower. (A) pAP1: AP1-GFP expression in 35S:LFY-GR plants. Plants were treated with mock solution, dexamethasone (Dex 10 µM) and dex in the presence of the gibberellin biosynthesis inhibitor paclobutrazol (PAC, 10 µM). Note the increase in AP1-GFP in young flower primordia of dex PAC treated plants. Treatment duration was 4 hours. Scale bar: 50 µm. (B) Relative AP1 expression based on qRT-PCR in mock treated or dexamethasone treated 35S:LFY-GR, 35S:RGA-GR and 35S:SPL9-GR plants. (C) AP1 induction in LFY-GR RGA-GR plants is independent of protein synthesis. AP1 induction relative to mock treated plants after treatment of 35S:LFY-GR/- and RGA-GR/- with the protein synthesis inhibitor cycloheximide (Cyc 100 µM), dexamethasone (Dex 10 µM) or dex plus cyc. (D) pRGA:RGA-GFP strongly associates with regulatory regions "b", "c", and "d" of the AP1 locus based on anti-GFP ChIP-qPCR in 25-day-old inflorescences. WT: control ChIP in untransformed wild type plants. NC: EIF4. Below: AP1 promoter domains and PCR fragments amplified. Very similar AP1 promoter association was observed for pRGA-RGA-HA (FIG. 4B). (E) Yeast-one-hybrid test. Left: Yeast growth under non-selective conditions. Middle and right: Yeast growth in the presence of the fungal inhibitor aureobasidin A (AbA). A yeast strain stain was engineered to contain in its genome a single copy of a 300 bp AP1 regulatory region, which includes the "d" region bound by RGA and SPL9 driving expression of the AbA resistance gene AUR1-C. Expression of SPL9 fused to the GAL4 activation domain (SPL9-AD) in this yeast strain conferred ability to grow on AbA (20 nM, 40 nM), while expression of RGA-AD or SPL9 (no AD) did not. Simultaneous expression of RGA-AD with SPL9 (no AD) dramatically enhanced the ability of the yeast to survive on AbA, suggesting that SPL9 recruited RGA-AD to the AP1 locus regulatory region. (F) Plants with increased LFY, SPL9 and DELLA protein levels form flowers immediately after the vegetative phase (essentially no cauline leaves are produced). Plotted are mean±SEM of the number of cauline leaves, a measure of the duration of the first inflorescence phase. Paclobutrazol (PAC, 1 µM); rSPL9: a microRNA insensitive version of SPL9. P values *<0.05, <0.01, *<$10^{-7}$ (Two-sided Students t-test). (G) Proposed model for the role of gibberellin in the biphasic transition to flower formation. An increase in gibberellin levels during the vegetative phase (V) causes the transition to the first inflorescence phase (I1) and upregulation of SPL proteins and LFY. LFY then triggers gibberellin catabolism at least in part by upregulating ELA1. After gibberellin levels are below a critical threshold, DELLA proteins re-accumulate, which potentiate the ability of SPL proteins and of LFY to upregulate AP1 and to trigger the switch to flower formation (second inflorescence phase (I2)). Arrow: onset of gibberellin catabolism.

DETAILED DESCRIPTION OF THE INVENTION

The invention relates generally to transgenic molecules for controlling plant growth and development. Specifically, the invention relates to transgenic molecules comprising a gibberellin associated floral fate inducer or gibberellin inhibitor operably linked to a promoter specific to flower primordium or lateral organ primordium. The invention also relates to transgenic plants having the transgenic molecules and methods for making such transgenic plants.

Gibberellin was known to promote the transition from vegetative development to the first inflorescence phase of reproductive development. Surprisingly and unexpectedly, the inventors of the instant application found that gibberellin inhibits the transition to flower formation. As a result, the inventors found that floral fate can be induced by inhibiting gibberellin.

In one aspect, provided herein is a recombinant nucleic acid molecule comprising: a transgenic nucleic acid sequence comprising a sequence encoding a floral fate inducer or gibberellin inhibitor operably linked to a promoter specific to flower primordium or lateral organ primordium.

In another aspect, provided herein is a recombinant nucleic acid molecule comprising: a first transgenic sequence and a second transgenic sequence, said first transgenic sequence comprising a nucleic acid sequence encoding a gibberellin activator operably linked to a vegetative stage specific promoter or lateral organ specific promoter and a second transgenic sequence comprising a nucleic acid sequence encoding a gibberellin inhibitor operably linked to a flower primordium specific promoter or a lateral organ primordium specific promoter.

Gibberellin inhibitor, as used herein, may refer to a molecule associated with inhibiting gibberellin or its synthesis, a gibberellin catabolism enzyme, a molecule associated with reducing gibberellin levels, a molecule associated with reducing gibberellin activity, a molecule that inhibits a gibberellin activator, a molecule associated with modulating gibberellin signal transduction, or a molecule associated with reducing gibberellin response. The terms "a sequence encoding a gibberellin inhibitor," as used herein, may refer to the nucleic acid sequence that encodes for the amino acid sequence of a gibberellin inhibitor protein or gene. Gibberellin inhibitor genes are well known in the art. In a particular embodiment, gibberellin inhibitor has the function of a floral fate inducer. Examples of such gibberellin inhibitor or floral fate inducer include, but are not limited to, LEAFY (LFY), EUI-LIKE P450 A1 (ELA1), DELLA protein (e.g., a stabilized DELLA, repressor of GA1-3 (RGA), ra1 guanine nucleotide dissociation stimulator-like (RGA-Like) 1, RGA-Like 2, RGA-Like 3, and GAI), squamosa promoter binding-protein-like 9 (SPL-9), P450 mono-oxygenase, GA2-oxidase, Gibberellin methyl transferase (Gamt) 1, Gamt 2, maize dwarf plant 8, maize dwarf plant 9, rice SLR1, tomato LeGAI, and grape GAL. Examples of gibberellin inhibitor or floral fate inducer may also include an inhibitor of a gibberellin activator, for example, but not limited to, ent-copalyl diphosphate synthase (CPS), ent-kaurene synthase (KS), ent-kaurene oxidase (KO), ent-kaurenoic acid oxidase (KAO), GA 13-oxidase (GA13ox), GA 20-oxidase (GA20ox), and GA 3-oxidase (GA3ox), CYP701A family gene, CYP88A family gene, Repression of Shoot Growth (RSG), GA insensitive dwarf (GID) 1, GID2. Additional examples of gibberellin inhibitor or floral fate inducer may include a gibberellin catabolism enzyme, for example, but not limited to, CYP714A family gene and CYP716D family gene.

The nucleic acid and amino acid sequences of the genes discussed herein are well known in the art and publicly available in genetic sequence databases. For example, GenBank accession numbers for the sequences of *Arabidopsis* LFY, ELA1, RGA, RGA-Like 1, RGA-Like 2, RGA Like 3, GAI, and SPL9 are: NM_125579; NM_122400; NM_126218; NM_105306; NM_111216; NM_121755; NM_101361; and NM_129782, respectively.

The invention also encompasses homologs, analogs, orthologs, functional fragments, functional variants, or functional derivatives of the sequences of the genes discussed herein. In some embodiments, the invention includes sequences that are 30%, 40%, 50%, 60%, 70%, 75%, 80%, 85%, 90%, 95%, 98%, 99%, or 100% identical to the sequences of the genes discussed herein. In one embodiment, the invention includes the sequences that are complementary to the sequences of the genes discussed herein. In another embodiment, the invention includes the sequences that hybridize, for example, under stringent conditions, to the sequences of the genes discussed herein. In a particular embodiment, the invention includes various crop plant sequences that correspond to or substantially similar to any *Arabidopsis* sequence discussed herein.

Gibberellin activator, as used herein, may refer to a molecule associated with enhancing gibberellin or its synthesis, a gibberellin biosynthesis enzyme, a gibberellin metabolism enzyme, a molecule associated with increasing gibberellin levels, a molecule that inhibits gibberellin inhibitor, for example, by using methods well known in the art (e.g., RNAi, microRNA, antisense RNA or peptide inhibitor related methods), a molecule associated with increasing gibberellin signal transduction, or a molecule associated with increasing gibberellin response. Examples of gibberellin activators include, but are not limited to, gibberellin activator GA 20-oxidase (e.g., GA20ox1, GA20ox2), GA 3-oxidase, GA 13-oxidase (GA13ox), ent-copalyl diphosphate synthase (CPS), ent-kaurene synthase (KS), ent-kaurene oxidase (KO), ent-kaurenoic acid oxidase (KAO), SLENDER1, SEC, scarecrow-like 3 (SCL3), and a regulator of DELLA activity, for example, SPINDLY and SECRET AGENT, CYP701A family gene, CYP88A family gene, Repression of Shoot Growth (RSG), GA insensitive dwarf (GID) 1, and GID2.

Flower primordium specific promoters and lateral organ primordium specific promoters are also well known in the art. Examples of flower primordium specific promoter or lateral organ primordium specific promoter include, but are not limited to, LFY promoter, ANT promoter, FIL promoter, FD promoter, BRANCHED promoter, AP1/FUL clade promoter, MP promoter, TMO3 promoter, maize WOX promoter, maize Indeterminate promoter, maize RS promoter, rice APO1 promoter, tomato AN promoter, grape VFL promoter, and maize ZFL1 and ZFL2 promoters.

Vegetative stage specific promoters are also well known in the art. Examples of vegetative stage specific promoter include, but are not limited to FLC, mir156 (e.g., maize mir156, tomato mir156, rice mir156, and grape mir156), tomato FA promoter and wheat RN1 promoter.

In another aspect, the invention provides a recombinant DNA construct having a gibberellin activator or inhibitor operably linked to a promoter of the invention. Recombinant DNA constructs can be prepared using methods well known to one of skilled in the art. In some embodiments, the recombinant DNA construct may include, for example, but are not limited to, additional regulatory elements, such as 5' leaders and introns for enhancing transcription, 3' untranslated regions (such as polyadenylation signals and sites), and DNA for transit or signal peptides. Constructs and vectors may also include a transit peptide for targeting of a gene to a plant organelle, for example, to a chloroplast, leucoplast or other plastid organelle. The expression cassettes or the construct of the invention may be included in a host cell, plant cell, seed, agricultural product or plant.

One of skilled in the art is well aware of the genetic elements that need to be present on the vector in order to successfully transform, select and propagate host cells containing the sequence of interest. The sequence of interest can be operably linked to one or more promoter sequences in the vectors of the invention.

The term "promoter," as used herein, may refer to a nucleic acid control sequence located upstream from the transcriptional start of a gene and which is involved in recognizing and binding of RNA polymerase and other proteins, thereby directing transcription of an operably linked nucleic acid. A plant promoter includes regulatory elements, which mediate the expression of a coding sequence segment in plant cells. Accordingly, a plant promoter need not be of plant origin, but may originate from viruses or micro-organisms, for example from viruses which attack plant cells. The plant promoter can also originate from a plant cell, e.g. from the plant which is transformed with the nucleic acid sequence to be expressed in the inventive process and described herein. The promoters upstream of the nucleotide sequences useful in the methods, constructs, plants, harvestable parts and products of the present invention can be modified by one or more nucleotide substitutions, insertions and/or deletions without interfering with the functionality or activity of either the promoters, the open reading frame (ORF) or the 3'-regulatory region such as terminators or other 3' regulatory regions which are located away from the ORF. It is furthermore possible that the activity of the promoters is increased by modification of their sequence, or that they are replaced completely by more active promoters, even promoters from heterologous organisms. For expression in plants, the nucleic acid molecule must, as described above, be linked operably to or comprise a suitable promoter which expresses the gene at the right point in time and with the required spatial expression pattern.

For the identification of functionally equivalent promoters, the promoter strength and/or expression pattern of a candidate promoter may be analyzed, for example, by operably linking the promoter to a reporter gene and assaying the expression level and pattern of the reporter gene in various tissues of the plant. Suitable well-known reporter genes include, for example, but are not limited to, beta-glucuronidase or beta-galactosidase, green fluorescent protein (GFP), and luciferase. The promoter activity can be assayed, for example, by measuring the enzymatic activity. The promoter strength and/or expression pattern may then be compared to that of a reference promoter (such as the one used in the methods of the present invention). Alternatively, promoter strength may be assayed by quantifying mRNA levels or by comparing mRNA levels of the nucleic acid used in the methods of the present invention, with mRNA levels of housekeeping genes such as 18S rRNA, using methods known in the art, such as Northern blotting with densitometric analysis of autoradiograms, quantitative real-time PCR or RT-PCR (See Heid et al., 1996 *Genome Methods* 6: 986-994).

The terms "operably linked," as used herein may refer to a functional linkage between the promoter sequence and the gene of interest, such that the promoter sequence is able to initiate transcription of the gene of interest.

In some embodiments, the invention provides one or more promoters, for example, tissue-specific promoters that drive constitutive gene expression. A "tissue-specific promoter" refers to a promoter that is transcriptionally active during most, but not necessarily all, phases of growth and development and under most environmental conditions, in at least one cell, tissue or organ. In an exemplary embodiment, either a tissue-specific or a constitutive promoter directs inducible expression, for example, ethanol inducible or steroid (e.g., ER and GR) inducible.

According to another aspect, the invention provides transforming a cell with the nucleic acid molecule or construct of the invention. The transfer of foreign genes into the genome of a plant is called transformation. Methods for transforming a plant cell with nucleic acids sequences are well known in the art. Transformation of plant species is now a fairly routine technique. As used herein the term "transformation" or "transforming" may refer to a process by which a foreign DNA, such as a DNA construct, including expression vector, enters and changes a recipient cell into a transformed, genetically modified or transgenic cell. Transformation may be stable, wherein the nucleic acid sequence is integrated into the plant genome and as such represents a stable and inherited trait, or transient, wherein the nucleic acid sequence is expressed by the cell transformed but is not integrated into the genome, and as such represents a transient trait. According to a preferred embodiment, the nucleic acid sequence of the present invention is stably transformed into a plant cell.

There are various methods of introducing foreign genes into both monocotyledonous and dicotyledonous plants (See Potrykus I 1991. *Annu Rev Plant Physiol Plant Mol Biol* 42, 205-225; Shimamoto K. et al., 1989. *Nature* 338, 274-276). Transformation methods may include, for example, but are not limited to, the use of liposomes, electroporation, chemicals that increase free DNA uptake, injection of the DNA directly into the plant, particle gun bombardment, transformation using viruses and microprojection.

Plant transformation methods are fully described in U.S. Patent Application Publications US 20110209247; US 20110113514; US 20100199371; US 20070079396; US 20080307541; US 20030028913; and US20030196219; and U.S. Pat. Nos. 5,015,580; 5,550,318; 5,538,880; 6,160,208; 6,399,861; 6,403,865; 5,635,055; 5,824,877; 5,591,616; 5,981,840 and 6,384,301, which are incorporated by reference herein in their entirety.

In one embodiment, the transformation can be performed by an *Agrobacterium*-mediated gene transfer. The *Agrobacterium*-mediated system includes the use of plasmid vectors that contain defined DNA segments which integrate into the plant genomic DNA. Methods of inoculation of the plant tissue vary depending upon the plant species and the *Agrobacterium* delivery system. The transformation can be performed with any suitable tissue explant that provides a good source for initiation of whole-plant differentiation (See Horsch et al., 1988. *Plant Molecular Biology Manual* A5, 1-9, Kluwer Academic Publishers, Dordrecht).

In one embodiment, the transformation can be performed by a direct DNA uptake. There are various methods of direct DNA transfer into plant cells. In electroporation, the protoplasts are briefly exposed to a strong electric field, opening up mini-pores to allow DNA to enter. In microinjection, the DNA is mechanically injected directly into the cells using micropipettes. In microparticle bombardment, the DNA is adsorbed on microprojectiles such as magnesium sulfate crystals or tungsten particles, and the microprojectiles are physically accelerated into cells or plant tissues.

The transgenic plant is then grown under conditions suitable for the expression of the recombinant DNA construct or constructs. The regeneration, development and cultivation of plants from single plant protoplast transformants or from various transformed explants is well known in the art (See Weissbach and Weissbach, In.: Methods for Plant Molecular Biology, (Eds.), 1988 Academic Press, Inc., San Diego, Calif.). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

Markers or other techniques, known to one of skilled in the art, can be used to determine whether the transgenic molecule is stably integrated into the genome of said plant.

The regenerated plants containing the foreign, exogenous gene that encodes a protein of interest can then be further propagated as is well known in the art. The particular method of propagation will depend on the starting plant tissue and the particular plant species to be propagated.

In one embodiment, the generated transformed plants are clonally propagated. In another embodiment, the generated transformed plants are propagated by classical breeding techniques. In a particular embodiment, the regenerated plants are self-pollinated to provide homozygous transgenic plants. Otherwise, pollen obtained from the regenerated plants is crossed to seed-grown plants of agronomically important lines, or pollen from plants of these important lines is used to pollinate regenerated plants. A transgenic plant of the present invention containing a desired polypeptide is cultivated using methods well known to one of skill in the art.

In a particular embodiment, transgenic plants can be observed or tested for whether the transgenic molecule is effective in inducing floral fate or its associated phenotypic trait in the transgenic plants.

Throughout this application a plant, plant part, seed or plant cell transformed with—or interchangeably transformed by—a construct or transformed with or by a nucleic acid is to be understood as meaning a plant, plant part, seed or plant cell that carries said construct or said nucleic acid as a transgene due the result of an introduction of said construct or said nucleic acid by biotechnological means. The plant, plant part, seed or plant cell therefore comprises said recombinant construct or said recombinant nucleic acid. Any plant, plant part, seed or plant cell that no longer contains said recombinant construct or said recombinant nucleic acid after introduction in the past, is termed null-segregant, nullizygote or null control, but is not considered a plant, plant part, seed or plant cell transformed with said construct or with said nucleic acid within the meaning of this application.

This invention also provides methods for manufacturing transgenic seed that can be used to produce a crop of transgenic plants with an enhanced trait resulting from expression of a stably-integrated recombinant DNA construct.

In another aspect, provided herein is a method for inducing a floral fate to improve reproductive development in a plant, the method comprising: applying a gibberellin inhibitor during the flower primordium developmental stage or after the termination of vegetative stage of said plant. As discussed above, gibberellin inhibitors are well known in the art. Small molecule gibberellin inhibitors (e.g., paclobutrazol or uniconazol) are also well known in the art. In a preferred embodiment, Small molecule gibberellin inhibitors (e.g., paclobutrazol or uniconazol) are applied at the flower primordium developmental stage or after the termination of vegetative stage of the plant. Gibberellin inhibitors can be applied to plants or plants can be treated by gibberellin inhibitors by suitable methods well known in the art. For example, treatments can be by spray, addition of growth medium, or injection into their parts (e.g., stems in fruit trees).

In another aspect, provided herein is a method for improving yield in a crop plant, the method comprising: applying a gibberellin or its activator during a vegetative stage of said crop plant; and applying a gibberellin inhibitor during the flower primordium developmental stage or after the termination of vegetative stage of said plant.

Any suitable gibberellin, known to one of skilled in the art, can be used. Examples of gibberellin, include, but not limited to, GA1, GA3, GA4, GA7, and GA20.

In another aspect, provided herein is a formulation for a plant growth, said formulation comprising a first composition and a second composition, said first composition comprising a gibberellin or its activator in combination with a fast release polymer component, wherein said first composition is capable of releasing said gibberellin or its activator soon after its application to a plant in vegetative stage; and said second composition comprising a gibberellin inhibitor in combination with a slow release or a delayed release polymer component, wherein said second composition is capable of releasing said gibberellin inhibitor later during a lateral organ primordium or a flower primordium developmental stage.

Fast release polymer components are well known in the art. Any suitable fast release polymer component can be used in the formulation. Also, slow release or delayed release polymer components are also well known in the art. Any suitable slow release or delayed release polymer components can be used in the formulation.

The term "plant," as used herein may relate to any monocot or dicot plant. Examples of monocot plant includes, but are not limited to, corn, wheat, rice, sugar cane, and banana. Examples of monocot plant includes, but are not limited to, soybean, beans, peas, lentils, peanuts, tomatoes, potatoes, cotton, and perennial fruit trees including grapes, apple, and orange.

Any reference including patents, patent applications, or scientific publications, cited herein, are incorporated by reference in their entirety.

The following examples are presented in order to more fully illustrate the preferred embodiments of the invention. They should in no way be construed, however, as limiting the broad scope of the invention.

EXAMPLES

Example 1

Gibberellin Acts Positively then Negatively to Control Onset of Flower Formation in *Arabidopsis*

The switch to reproductive development is biphasic in many plants, a feature important for optimal pollination and yield. We show that dual opposite roles of the phytohormone gibberellin underpin this phenomenon in *Arabidopsis*. While gibberellin promotes termination of vegetative development, it is inhibitory for floral fate. To overcome this effect, the transcription factor LEAFY induces expression of a gibberellin catabolism gene, consequently increased LEAFY activity causes reduced gibberellin levels. This allows accumulation of gibberellin-sensitive DELLA proteins. The DELLA proteins are recruited by SQUAMOSA PROMOTER BINDING PROTEIN LIKE transcription factors to regulatory regions of the floral commitment gene APETALA1 and promote APETALA1 upregulation and floral fate synergistically with LEAFY. The two opposing functions of gibberellin may facilitate evolutionary and environmental modulation of plant inflorescence architecture.

Figure 1:
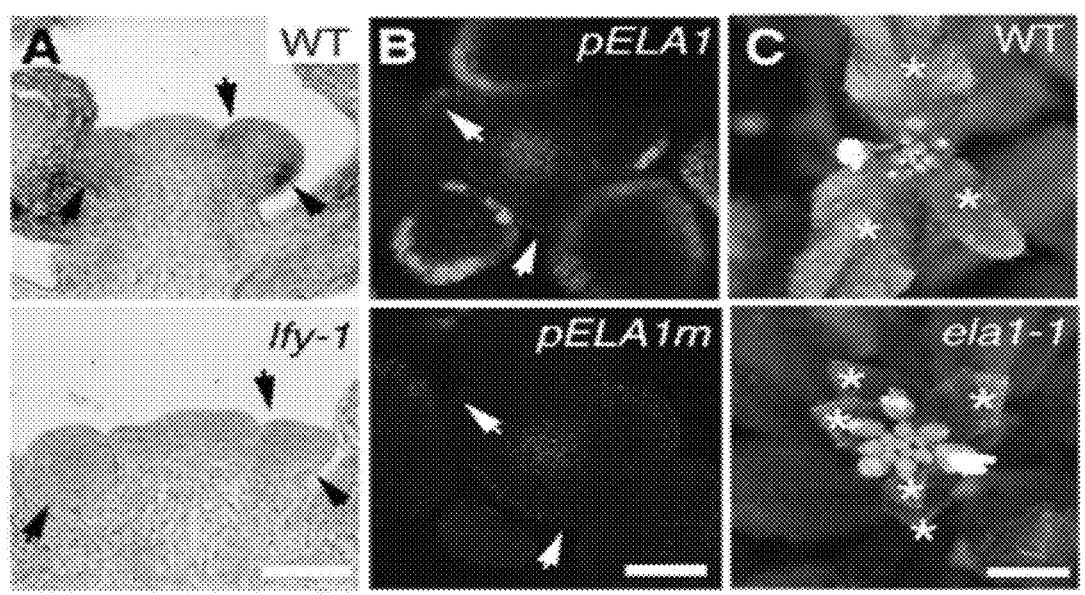
FIG. 1. ELA1 is a direct LFY regulated target and promotes flower formation. (A) ELA1 in situ hybridization in wild-type (top) and lfy-1 (bottom) inflorescences. (B) GFP reporter expression driven from wild-type (top) or LFY binding site mutated (bottom) ELA1 promoter. (A, B) Arrows: young floral primordia. (C) Top view of wild type (top) and ela1-1 mutant (bottom) inflorescences. The average number of cauline leaves and branches formed was significantly ($P<10^{-5}$, two-sided Student's t-test) higher in ela1-1 (4.6±0.1) than in the wild type (2.8±0.1). Asterisks: cauline leaves subtending branches. Scale bars: 50 µm (A, B), 5 mm (C).
Figure 6:
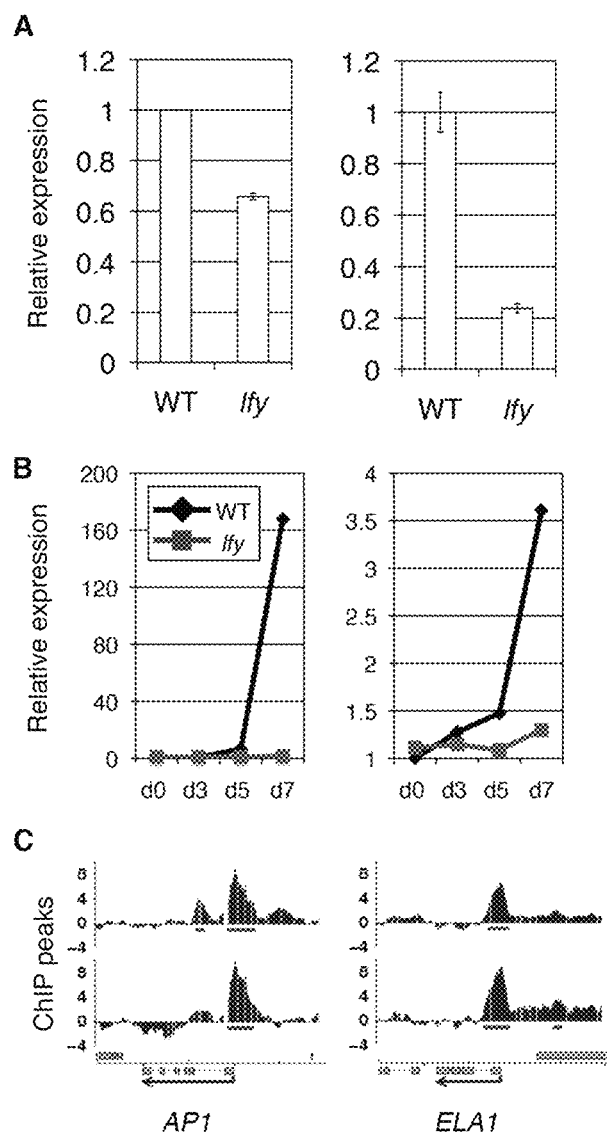
FIG. 6. ELA1 is a direct LFY-regulated target gene. 164 genes were identified whose regulatory regions were significantly bound by LFY (FDR<0.05) and whose expression was significantly altered in lfy null mutant compared to wild type inflorescences (adjusted P value <0.005). Among these, we selected genes with (i) significantly (adjusted P value <0.005) changed expression upon induction of LFY-GR and (ii) significantly (adjusted P value <0.005) changed expression during the onset of reproduction at the shoot apex (from day 7 to day 21) and (iii) significantly (adjusted P value <0.005) changed expression during photoperiod induction that was LFY-dependent (adjusted P value <0.01). The known direct LFY target AP1 and the cytochrome P450 encoding gene CYP714A1, also called EUI-LIKE P450 A1 (ELA1) fulfilled all criteria. (A) Expression of AP1, and ELA1 in 21-day-old wild type or lfy mutant inflorescences (ATGE_29, ATGE_47). For each gene expression values were normalized over the mean expression value observed in the wild type. (B) Photoperiod induction of AP1 and ELA1 in the presence of absence of LFY. For each gene expression values were normalized over the mean expression value of wild type at day 0 (D0) (C) LFY recruitment to AP1 and ELA1 regulatory regions. Tracks: moving average t-statistic (20 kb window) for LFY binding at the time of the formation of the first flower (top) and in inflorescences (bottom), based on ChIP-chip. Horizontal red bars: significantly bound regions (FDR<0.05).
Figure 7:
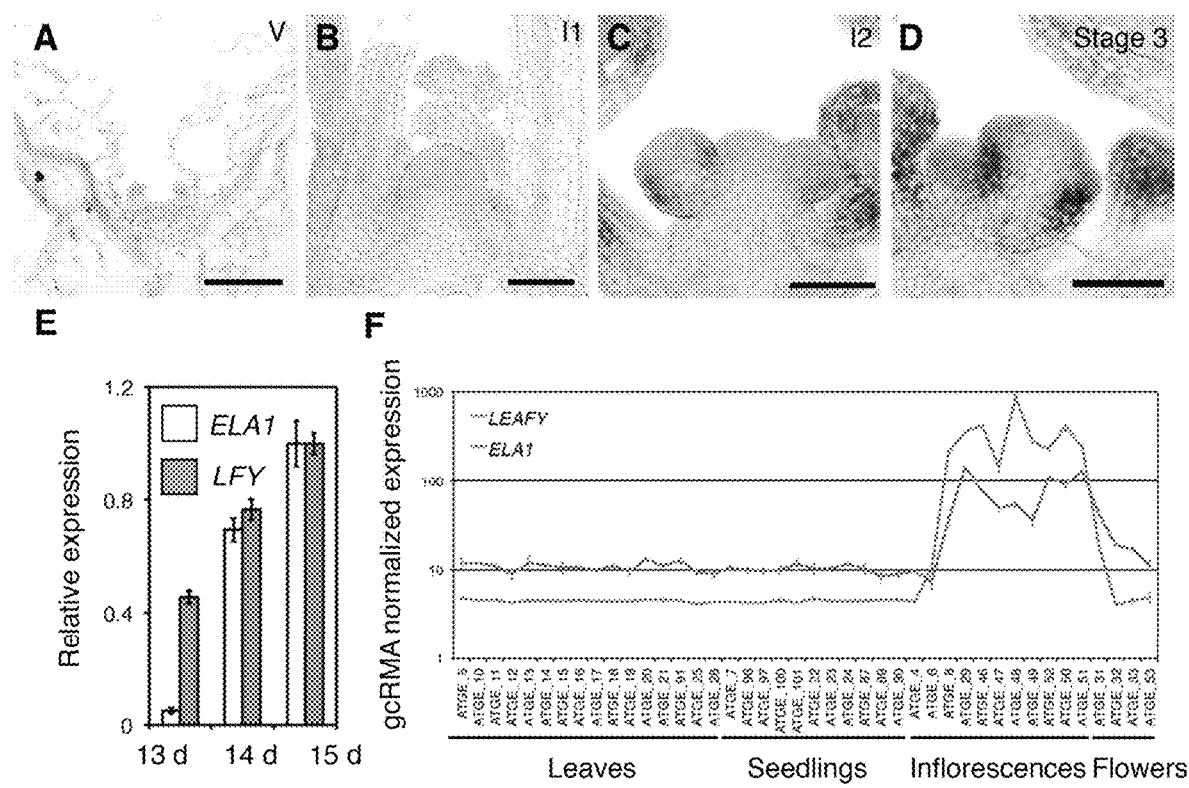
FIG. 7. Expression of ELA1 is developmentally regulated. (A-D) In situ hybridization to detect ELA1 message accumulation in the shoot apex during the vegetative phase (day 5, (A)), the first inflorescence phase (I1, day 12, (B)), the second inflorescence phase (I2, (C)), and in flowers (Stage 3, (D)). Scale bars: 50 µm. (E) qRT-PCR of ELA1 and LFY to assess steady-state mRNA accumulation in wild-type plants in long day photoperiods. ELA1 expression is upregulated subsequent to that of LFY. Stages assayed include the first inflorescence phase (day 13) to the second inflorescence phase (day 15). (F) Developmental regulation of LFY and ELA1 expression based on published transcriptome data. ELA1 and LFY are not expressed in full-expanded leaves or in above-ground tissues of young seedlings. ELA1 and LFY are highly expressed in inflorescences.
Figure 8:
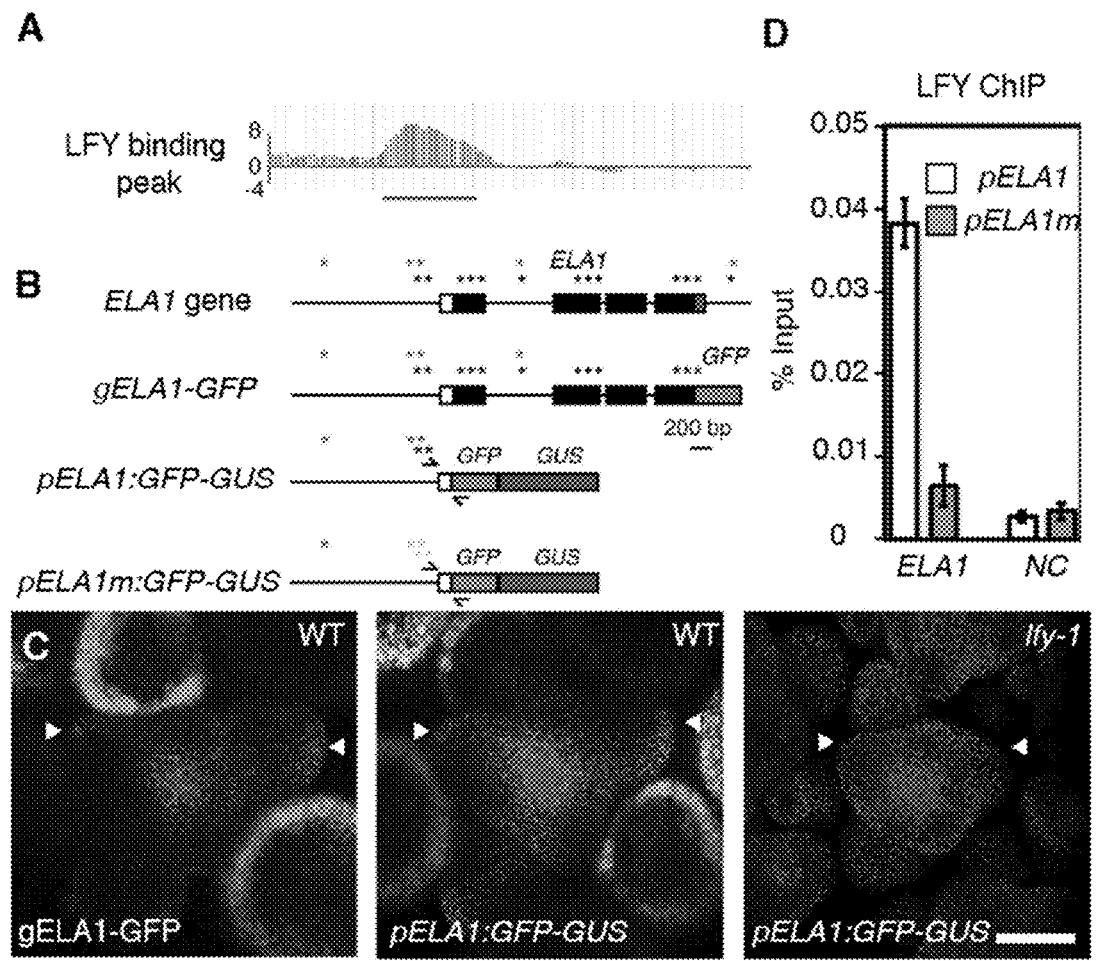
FIG. 8. LFY activity and LFY-bound cis elements are required for ELA1 expression in newly formed flower primordia. (A) The LFY binding peak maximum is close to the ELA1 transcription start site (at −266 bp) based on ChIP-chip. (B) Reporter constructs generated. Top: ELA1 gene. Black line denotes intergenic region and introns. White box denotes 5'UTR. Grey box indicates 3'UTR. Black boxes represent exons. Below: gELA1-GFP. Genomic ELA1 fusion to GFP. Below: pELA1:GFP-GUS. ELA1 promoter: reporter fusion. Bottom: pELA1m:GFP-GUS. ELA1 promoter with 4 LFY binding motifs mutated. Two of the motifs are primary LFY binding motifs (red asterisks): TTTCTATCTTTCGGTCCCTCT (SEQ ID NO: 1), and GTATGGACCGATAGACAAATT (SEQ ID NO: 2). The remaining two motifs are secondary LFY binding motifs (black asterisks): GGACCGATAGACA (SEQ ID NO: 3) (nested within the primary motif 2), and AGCC-CATGTGTCT (SEQ ID NO: 4). The residues underlined were replaced with aagctt in pELA1m. Functional depth (FD) is a discriminative score for modeling transcription factor binding affinity that ranges between 0 (lowest) and 1 (highest). FD scores for the 4 LFY bindings motifs are: motif 1: 0.84 (unchanged), 0.73 (mutated); motif 2: FD 0.81 (unchanged), 0.63 (mutated); motif 3: FD 0.77 (unchanged), 0.64 (mutated) and motif 4: FD 0.81 (unchanged), 0.63

To gain insight into the regulation of the transition from branch to floral fate in the lateral primordia of the inflorescence, we analyzed public genome-wide binding and expression data and identified genes that are direct targets of the LEAFY (LFY) transcription factor. LFY promotes flower formation. We identified for further study the EUI-LIKE P450 A1 (ELA1) gene (FIG. 6), which encodes a cytochrome P450. ELA1 expression was very low in vegetative tissues, but increased when flowers formed (FIG. 7). Based upon in situ hybridization and reporter studies, ELA1 was initially expressed on the abaxial side of incipient flower primordia and later along their entire circumference (FIGS. 1A and 7). ELA1 expression was dependent on the presence of functional LFY and on the presence of LFY-bound cis-elements in the ELA1 regulatory region (FIGS. 1B and 8). To determine whether ELA1 is required for the switch to flower formation in long day photoperiods, we obtained three mutant alleles (FIG. 9). Consistent with its very low expression in vegetative tissues, ela1 mutants did not alter the duration of the vegetative phase (FIG. 9). By contrast, loss-of ELA1 function significantly delayed flower formation (FIGS. 1C and 9). Thus, ELA1 promotes floral fate in lateral organ primordia of the inflorescence.

Figure 2:
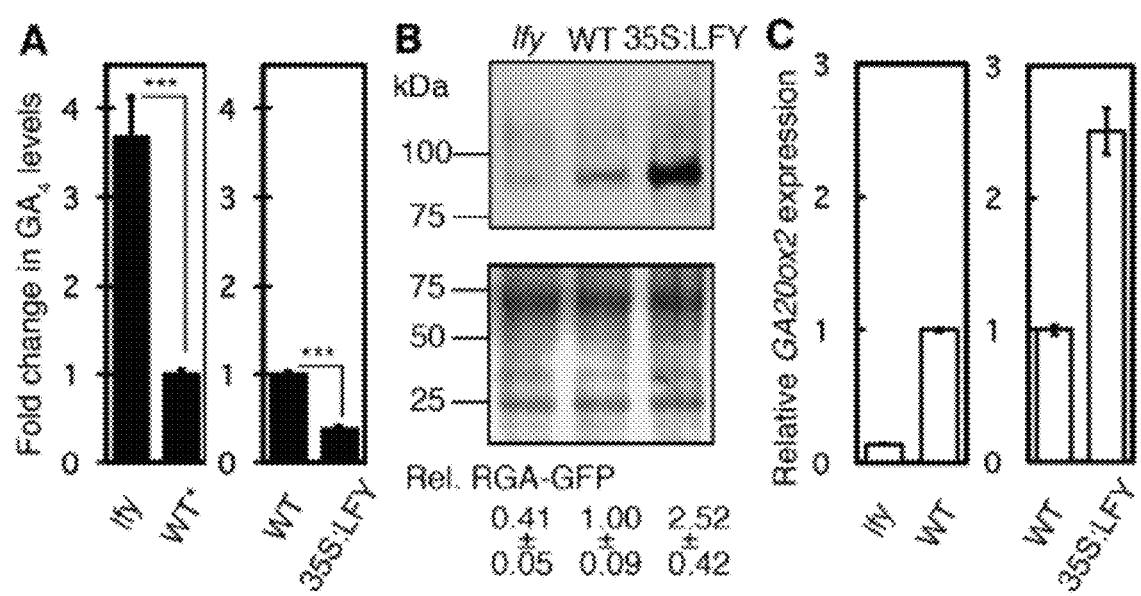
FIG. 2. LFY causes a reduction of gibberellin levels in the inflorescence. (A) LC-MS/MS-based determination of the level of gibberellin A4 ($GA_4$) in lfy null mutant and in 35S:LFY overexpressing relative to control inflorescences. Asterisks (***): $P<10^{-3}$ based on two-sided Student's t-test. (B) Top: Anti GFP Western of lfy null mutant, wild-type (WT), or 35S:LFY inflorescences expressing pRGA:RGA-GFP. Center: Ponceau S stained membrane. Bottom: Band intensity in three biological replicates (P=0.007 lfy versus WT, P=0.008 35S:LFY versus WT; two-sided Student's t-test). (C) mRNA abundance of the GA biosynthesis gene GA20ox2 in lfy, wild-type, and 35S:LFY inflorescences. Mean±SEM are shown.

ELA1 functions in catabolism of bioactive gibberellins that are not hydroxylated at the carbon 13 position, such as gibberellin A4 ($GA_4$) (FIG. 10). Through upregulation of ELA1, LFY may reduce the levels of $GA_4$ during flower formation. Indeed, analysis of $GA_4$ levels by mass spectrometry after liquid chromatography revealed that this hormone is elevated in lfy null mutants and reduced in transgenic plants overexpressing LFY (FIGS. 2A and 11). Presence of bioactive gibberellin leads to degradation of DELLA proteins and triggers transcriptional repression of gibberellin biosynthesis genes including GIBBERELLIN 20 OXIDASE 2 (GA20ox2). Consistent with their elevated levels of $GA_4$, lfy inflorescences had reduced levels of the DELLA protein REPRESSOR OF GA1-3 (RGA) and of GA20ox2 mRNA. In contrast, LFY over-expressing inflorescences had elevated levels of RGA protein and GA20ox2 mRNA, relative to wild type plants (FIGS. 2B, C, and 11). Moreover, removal of ELA1 activity from 35S:LFY plants restored GA20ox2 mRNA to wild-type levels (FIG. 11). In agreement with their altered gibberellin levels, the Gene Ontology term "response to gibberellin stimulus" was significantly enriched (adjusted P-value <0.0005) among genes differentially expressed in lfy mutants or LFY overexpressing plants (FIG. 11), in agreement with their altered gibberellin levels. Finally, LFY over-expressing plants displayed phenotypes characteristic of gibberellin deficient mutants, such as reduced height and increased chlorophyll content, that were partly rescued by application of exogenous gibberellin (FIG. 11). The data indicate that LFY directs a reduction of gibberellin levels in inflorescences.

In *Arabidopsis*, gibberellin promotes the transition from vegetative development to the first inflorescence phase of reproductive development. However, our observations suggest that gibberellin may actually inhibit the transition to flower formation. This result was unexpected because in general mutants that delay onset of the first inflorescence phase also delay flower formation, while those that accelerate onset of the first inflorescence phase also accelerate flower formation (FIGS. 3A and 12). We therefore examined the effect of altered gibberellin levels or response on these two transitions. Under long-day conditions, mutants deficient in gibberellin biosynthesis or gibberellin response produced more rosette leaves (delayed onset of the first inflorescence phase), but fewer branches and cauline leaves (accelerated flower formation FIGS. 3B and 12). Likewise, plants treated with the gibberellin biosynthesis inhibitor paclobutrazol had more rosette leaves but fewer branches and cauline leaves (FIG. 12). By contrast, plants treated with exogenous gibberellin formed fewer rosette leaves and more branches and cauline leaves (FIGS. 3C and 12). We then decreased the gibberellin response selectively in lateral organ primordia of the inflorescence, by expressing a negative gibberellin response regulator (the stabilized DELLA protein rgl1) from the LFY promoter. This had no effect on the duration of the vegetative phase, but significantly accelerated flower formation (FIGS. 3D and 13). These results demonstrate that whereas gibberellin promotes the transition from vegetative to inflorescence development, it inhibits flower formation.

Reduced gibberellin levels may increase the competence of lateral organ primordia to adopt a floral fate by enhancing their responsiveness to LFY. To test this hypothesis, we employed a constitutively expressed version of LFY fused to the rat glucocorticoid receptor hormone binding domain (GR), which enables control of LFY activity by dexamethasone. We also took advantage of the observation that the direct LFY target APETALA1 (AP1) is only expressed in flower primordia, which makes AP1 expression a good proxy for floral competence. Simultaneous treatment of plants expressing LFY-GR with dexamethasone and the gibberellin biosynthesis inhibitor paclobutrazol caused increased production of AP1 in young flower primordia (FIGS. 4A and 13), relative to treatment with either paclobutrazol or dexamethasone alone. Via its inhibition of gibberellin biosynthesis, paclobutrazol promotes accumulation DELLA proteins. In agreement with this, dexamethasone treatment of plants expressing both a constitutively expressed DELLA protein fused to GR (RGA-GR) and LFY-GR also caused an increase in AP1 expression (FIGS. 4A and 13). The slightly lower expression of AP1 in RGA-GR LFY-GR plants treated with dexamethasone compared to LFY-GR plants treated with dexamethasone and paclobutrazol may be explained by the ability of paclobutrazol to stabilize multiple DELLA proteins or by degradation of RGA-GR due to the presence of endogenous gibberellin. Although DELLA proteins are best known for their roles in transcriptional repression, they can also activate transcription. Using ChIP-qPCR, we found that a tagged version of RGA expressed from its own promoter associated with several regulatory regions in the AP1 locus (FIGS. 4B and 13). Moreover, dexamethasone activation of RGA-GR LFY-GR plants in the presence of protein synthesis inhibitor also caused increased AP1 induction (FIG. 13). We conclude that the DELLA protein RGA potentiates LFY activity and directly promotes the transcription of AP1.

DELLA proteins lack DNA binding domains and are thought to be recruited to target loci by sequence specific transcription factors. The regulatory regions of the AP1 locus occupied by RGA were similar to those occupied by a known transcriptional activator of AP1, the miR156 target SQUAMOSA PROMOTER BINDING PROTEIN LIKE 9 (SPL9) (FIG. 4B). SPL9 can physically interact with DELLA proteins. We therefore next examined the possibility that RGA promotes AP1 transcription in association with SPL proteins. The AP1 induction by dexamethasone plus paclobutrazol treatment of LFY-GR was reduced when we simultaneously depleted SPL proteins with an ethanol inducible version of miR156 (FIG. 4C), suggesting that SPL proteins contribute to this effect. In agreement with this interpretation, concurrent activation of constitutively expressed SPL9 fused to GR (SPL9-GR) and LFY-GR also led to increased AP1 induction (FIG. 4C). The synergistic effect of SPL9-GR and LFY-GR on AP1 induction most likely requires the presence of DELLA proteins, since it was strongly reduced after application of exogenous gibberellin (FIG. 4C). In addition, SPL proteins were necessary for recruitment of RGA to the AP1 regulatory region both in plants and in yeast-one-hybrid assays (FIGS. 4D and 13). Finally, increased activity of LFY, SPL9 and DELLA proteins caused flower formation immediately after termination of the vegetative phase (FIGS. 4E and 13). We conclude that SPL9 recruits DELLA proteins such as RGA to the AP1 locus where they induce AP1 expression and promote the transformation of lateral primordia into flowers (FIG. 4F).

We reveal a mechanism for sequential coupling of the biphasic transition to reproductive competence in *Arabidopsis thaliana*. This mechanism is based on an increase and a subsequent decrease in hormone levels. Elevated gibberellin promotes termination of the vegetative phase and increases expression of genes encoding transcription factors such as the SPLs and LFY (FIG. 13). The subsequent reduction in gibberellin levels allows re-accumulation of transcriptional co-regulators, the DELLA proteins, which potentiate the ability of SPL9 (directly) and LFY (indirectly) to induce AP1 and to trigger the onset of flower formation (FIG. 13). LFY initiates the reduction in gibberellin levels—which results in increased DELLA accumulation—at least in part by inducing expression of the gibberellin catabolism enzyme ELA1.

Our findings may help explain the previously paradoxical observation that gibberellin acts positively in the switch to reproductive development in most plants but negatively in some woody plant species, such as grapevine. In addition, our data make gibberellin a prime candidate for a 'branching' factor predicted by mathematical modeling of inflorescence architectures. Finally, our results indicate that the degree of inflorescence branching, which determines seed yield and thus reproductive success, could be adjusted by altering gibberellin accumulation before the inflorescence forms or the rate of gibberellin catabolism thereafter.

Materials and Methods
Plant Materials

Plants were grown at 23° C. in a 16 h light/8 h dark cycle. The following plant lines were previously described: lfy-1 null and lfy-2 hypomorph mutants; lfy-6 null mutants; 35S:LFY-GR; 35S:LFY; ga1-3; gai; pRGA:RGA-GFP; pRGA:RGA-HA; ga1-3 rgl2-1 rga-2 35S:RGA-GR; pSPL9:rSPL-FLAG; 35S:AlcR pAlcA:mir156f; and 35S:SPL9-GR and pAP1:AP1-GFP. The ela1-1 and ela1-3 alleles were obtained from the SALK T-DNA insertion line collection (SALK_005782, and SALK_049907, respectively). The ela1-2 allele was obtained from the SK collection (SK6964). Genotyping primers for the ela1 mutants are listed in Table 1. Most plants were in the Columbia background except for 35S:LFY-GR, pRGA:RGA-GFP, and lfy-6 mutants, which were in the Landsberg erecta background. To avoid comparisons of plants in different ecotype backgrounds, we performed crosses between homozygous transgenic plants and conducted all subsequent analyses in the F1 population. For single transgenic controls, we performed crosses to the wild type strain that would result in the same ecotype combination as the crosses between the two transgenic lines. Statistical analyses were performed on plant phenotypes that are normally distributed. The population size was determined by expedience (tissue or plant amount that could reasonably be obtained).

Hormone and Inhibitor Treatments

For hormone and other treatments, dexamethasone (dex) and gibberellin A3 ($GA_3$) were dissolved in ethanol, while paclobutrazol (PAC) was dissolved in methanol, and stored at −20° C. prior to use. For mock treatment, 0.01% ethanol (EtOH) with 0.01% Silwet L-77 was used as control. To compare gibberellin levels in lfy-6 null mutants that lack or have restored LFY activity (WT*), soil-grown lfy-6 35S:LFY-GR plants were treated just after bolting by spraying them once with mock solution or 10 µM dexamethasone, respectively (FIG. 2A). To count cauline leaf numbers in the severely dwarfed ga1-3 mutant background (FIG. 3B) internode elongation was induced after the plants had started to make flowers by treating them twice (one day apart) with 100 µM gibberellin. For gibberellin treatment in wild type to examine the number of rosette and cauline leaves formed (FIG. 3C), soil-grown plants were treated from day 8 to day 16 by spraying them with 100 µM gibberellin every other day. For gibberellin treatment of 35S:ELA1 plants, soil-grown plants were treated from day 5 to day 20 by spraying them with 100 µM gibberellin every fifth day (figure S6). For gibberellin treatment in 35S:LFY to monitor plant height and chlorophyll content (figure S7), soil-grown plants were treated from day 10 to day 16 by spraying them with 100 µM gibberellin every other day. For paclobutrazol treatment in wild type to examine the number of rosette and cauline leaves formed (figure S8), wild-type plants were first germinated on MS plates. After 4 days plants were transferred either to MS plates containing 1 µM paclobutrazol or to control MS plates and grown for 6 more days. At day 10, the plants were transplanted to soil. For test of AP1 induction in single or double hemizygous transgenic lines (FIG. 4A, C, and figure S9) treatments were performed by spraying 16-day-old plants grown on plates once with 10 µM dexamethasone and/or 10 µM paclobutrazol. Tissues were harvested after 4 hours. 16-day-old 35S:LFY-GR/- 35S:RGA-GR/- plants were sprayed with 10 µM dexamethasone and/or 100 µM cycloheximide (figure S9). Tissues were harvested after 4 hours. For test of AP1 induction after LFY-GR activation in the presence of PAC in conditional spl mutants (FIG. 4C), paclobutrazol and dexamethasone were dissolved in methanol, since methanol does not activate AlcR (41). 16-day-old 35S:AlcR pAlcA:mir156f/- 35S:LFY-GR/- plants were sprayed with 10 µM dexamethasone plus 10 µM paclobutrazol and exposed to ethanol vapor or water control. Tissues were harvested after 4 hours. For ethanol vapor (or control) treatment, an open PCR tube filled with 100 µl absolute EtOH (or water) was placed in the center of petri plates on which the 35S:AlcR pAlcA:mir156f/- 35S:LFY-GR/- plants were growing. Plates were sealed with parafilm. For RGA-HA ChIP in 35S:AlcR pAlcA:mir156f (FIG. 4D), soil-grown plants were treated from day 12 to day 16 every other day with ethanol vapor (or water control) for 4 hours. For test of the number of rosette or cauline leaves produced under conditions of increased DELLA accumulation/activity (FIG. 4E), WT, 35S:LFY/-, pSPL9:rSPL9-FLAG/-, and 35S:LFY/- pSPL9:rSPL9-FLAG/- were first germinated on MS plates, followed by transfer to MS plates containing 1 µM paclobutrazol or to control MS plates from day 4 to day 10 of age. At day 10, the plants were transplanted onto soil.

Transgenic Plants

For gELA1-GFP and pELA1:GUS-GFP constructs, the ELA1 locus including 1.6 kbp upstream of the translational start site and excluding the translation termination codon, or the 1.6 kbp ELA1 promoter region were PCR amplified using the BAC clone (F6A4) as a template, sequenced, and Gateway cloned into pGWB4 (42) and pBGWF7 (42, 43), respectively. For the LFY binding site mutated ELA1 promoter construct, mutations were introduced into the pELA1 construct by site directed mutagenesis. For primers used see Table 1. For the 35S:ELA1-GFP construct, the ELA1 cDNA excluding the translation termination codon was PCR amplified, sequenced, and Gateway cloned into pGWB5 (42). For pLFY:rgl1, pLFY fragment was amplified and TA-cloned into pGEM-T Easy (Invitrogen), vector (pLFY-pGEM-T). rgl1 (also called rgl1delta17) is a gibberellin insensitive version of the DELLA protein RGL1 (44). The rgl1 fragment was amplified by PCR with primer sets containing PstI and SalI sequences and cloned into pLFY-pGEM-T. pLFY:rgl1 was PCR amplified, Gateway cloned into pGWB1 (42) and sequenced. All constructs were transformed into wild-type plants by floral dip. Representative lines were chosen and characterized further. For cloning primers see Table 1.

Expression Analyses and Chromatin Immunoprecipitation (ChIP)

For qRT-PCR, RNA was isolated form entire plants after the switch to reproduction using TRIzol reagent (Invitrogen) and RNeasy Mini kits (Qiagen) and processed as previously described (45). Briefly, cDNA was reverse-transcribed using the Superscript III Kit (Invitrogen). Quantitative real-time PCR was performed using Power SYBR green mastermix (Applied Biosystems). The mean and standard error were determined using three technical replicates from one representative experiments. Two to three independent experiments were performed. Gene-specific signals were normalized over those of the EUKARYOTIC TRANSLATION INITIATION FACTOR 4A-1 (EIF4; At3g13920) or TUBULIN 2 (TUB2; At5g62690). For primers used see Table 1.

In situ hybridization was performed on dissected inflorescence apices as previously described (5, 46, 47). The ELA1 probe consisted of basepairs 112 to 1512 (TSS=1). Probes were cloned into pGEM-T Easy (Promega). Antisense ELA1 probe was digested with NcoI and transcribed with the T7 polymerase. The Riboprobe Combination System (Promega) and DIG RNA labeling mix (Roche, Branchburg, N.J., USA) were used for probe synthesis. In situ sections are from the same slide and were incubated for the same duration with the antisense ELA1 probe.

ChIP was performed as previously described (5) on inflorescence apices after the switch to reproduction. The following antisera were used: anti-GFP antibody (A6455; Invitrogen), anti-FLAG antibody (F3165; Sigma), anti-HA antibody (12CA5; Roche) and anti-LFY antibody (32). To estimate transcription factor occupancy on DNA, we computed the ratio of ChIP over input DNA (% Input) by comparing the reaction threshold cycle for each the ChIP sample to a dilution series of the corresponding input sample. This procedure was applied to both wild-type plants and plants expressing the transgene. The values computed for the transgenic plants were normalized over those observed in the wild type to obtain the ChIP fold-change. The mean and standard error of the mean were determined using three technical replicates of one representative experiment. Two to three independent experiments were performed. To test LFY binding to pELA1 and pELA1m, a 5' ELA1 specific and a 3' transgene specific primer were used for amplification. The fragment amplifies a region 100 bp downstream of the maximum LFY binding peak in pELA1. Since this PCR product cannot be amplified from the wild type, we normalized the % input observed over the ChIP yield observed for the negative control locus (EIF4A (At3g13920) promoter). Two independent experiments were performed. All ChIP primers are listed in Table 1.

Microscopy

For imaging of GFP fluorescence, inflorescence apices were dissected to remove older flowers and imaged using a Leica confocal microscope (Leica, LCS SL) equipped with an argon-krypton ion laser with the appropriate filter sets for visualizing GFP. Images are maximum projection of z-stacks that include the initiating flower primordia. The same offset and gain settings were used for all plants for which signal intensity was directly compared (i.e. those carrying the same transgene (s) but subjected to different treatments or present in a different genetic background). At least 10 inflorescences were prepared for each genotype and representative images are shown.

Chlorophyll Measurement

Total chlorophyll levels were measured using N, N'-dimethylformamide (DMF) extraction and spectrophotometric quantification (48). Discs (d=1.0 cm) from the fifth leaf of plants of the same age were placed into 1.5 ml tube containing DMF. n=20. Tubes were incubated overnight on a horizontal shaker. The absorbance at 646.8 and 663.8 nm was measured in 1.00 cm cuvettes on a Beckman model DU640D spectrophotometer. Total chlorophyll was computed as reported previously (48). (Chls a+b (µM)=19.43 $A_{646.8}$+8.05 $A_{663.8}$)

Yeast One-Hybrid Studies

The yeast one-hybrid assay was performed using Clontech's Matchmaker Gold Yeast One-Hybrid Library Screening System. For the bait construct, a PCR-amplified 300 bp genomic DNA fragment containing the "d" region of the AP1 promoter (FIG. 4B) was cloned into the pAbAi vector using SacI and XhoI restriction sites added to the linker, followed by sequencing. For the prey constructs, the SPL9 and RGA cDNA were PCR amplified, sequenced, and cloned into pDEST32 and DEST22 (containing GAL4-BD and GAL4-AD), respectively. Primers used for amplification are listed in Table 1. The bait was integrated into the genome of the Y1H Gold yeast strain (Clontech) by homologous recombination to generate a bait specific reporter strain. The resulting yeast integrants were co-transformed with RGA-GAL4 transactivation domain (GAL4 AD) fusion protein and SPL9. SPL9-GAL4AD served as a positive control. Empty vector (EV) was used as a negative control. Yeast containing the proximal pAP1 region and two prey vectors were plated in 10-fold serial dilutions on control plates without selective agent or on plates containing 20 or 40 ng/ml of aureobasidin A (AbA) to test for transactivation of the AUR-1C gene. Only when a SPL9 and RGA-GAL4AD or SPL9-GAL4AD were present was AUR-1C expression activated, leading to resistance to the antifungal antibiotic AbA.

Western Blotting

For RGA-GFP protein quantification, crude protein extracts were prepared from 5 inflorescences ground in ice cold 1.5 ml eppendorf tubes in 50 µl 2×SDS sample buffer. After the debris was removed by centrifugation, the samples were boiled and 25 µl of each sample was run on a 4-15% gradient gel. Prior to blocking and antibody incubation, the transfer membrane was stained with Ponceau S and photographed.

Rabbit polyclonal anti-GFP (Cell Signaling; #2555) and anti-rabbit HRP conjugate (1:2,000 diluted) were used as primary and secondary antibodies, respectively. Detection was performed using the ECL plus detection kit (Amersham Biosciences). Three independent experiments were performed. Image J was used to quantify signal intensity. For Ponceau S stain of the Western membrane the most prominent band was quantified.

Gibberellin Measurements

Plants were grown on soil and inflorescences were harvested just after bolting. 3 independent biological replicates were generated at two different time points (Total n=6). The tissue was frozen in liquid nitrogen and stored at −80° C. Approximately 300 mg (fresh weight) of inflorescence tissue from each line was lyophilized (Freezone 4.5, LAB-CONCO) to yield 30 mg dry weight. Lyophilized plant materials (20-50 mg dry weight) were ground in 3 mL of 80% (v/v) acetone containing 1% (v/v) acetic acid, and [17,17-$^2H_2$] GAs (300 pg each) were added as internal standards. This mixture was incubated for 12 h at 4° C. and then centrifuged at 3000 g for 20 min at 4° C. The supernatant was concentrated to dryness, and dissolved in 0.5 mL of aqueous acetonitrile (1:1, v/v). The solution was partitioned against an equal volume of n-hexane, and the n-hexane phase was discarded. After the removal of acetonitrile by evaporation in vacuo, the pH was adjusted to 8.0 with 500 mM dipotassium phosphate. The sample was loaded onto a polyvinylpyrrolidone (PVP, 500 mg; Tokyo Kasei, Japan) cartridge, and eluted with 3 mL of 500 mM potassium phosphate buffer. The pH of this eluate was adjusted to 3.0 with HCl, and loaded onto a reverse-phase cartridge (Oasis HLB, 60 mg; Waters). After washing with 3 mL of water containing 1% acetic acid, GAs were eluted with 6 mL of 80% acetonitrile containing 1% acetic acid. The eluate was dried, dissolved in methanol, and then loaded onto an ion-exchange column (Bond Elut DEA, 100 mg; Agilent). GAs were eluted with 3 mL of methanol containing 1% acetic acid after washing with 3 mL of methanol. The eluate was dried, dissolved in chloroform:ethylacetate=1:1 (v/v) containing 1% acetic acid, and then loaded onto a SepPak silica cartridge (100 mg; Waters). GAs were eluted with 3 mL of chloroform:ethylacetate=1:1 (v/v) containing 1% acetic acid. The eluted GA-containing fraction was concentrated to dryness, dissolved in 20 µL of water containing 1% acetic acid, and then subjected to LC-MS/MS analysis.

The LC-MS/MS system consisted of a quadrupole/time-of-flight tandem mass spectrometer (Triple TOF 5600, AB SCIEX) and an Nexera HPLC system (SHIMADZU) equipped with a reverse-phase column (Acquity UPLC BEH-Phenyl; 1.7 μm, 2.1×50 mm; Waters). LC separations were performed at a flow rate of 400 μL/min using the following program with solvent A (water containing 0.01% [v/v] acetic acid) and solvent B (acetonitrile containing 0.05% [v/v] acetic acid): an isocratic flow with 3% of B for 30 sec, a linear gradient of B from 3% to 20% over 2.5 min, a linear gradient of B from 20% to 40% over 5 min, an isocratic flow with 40% of B for 2 min, a liner gradient of B from 40% to 98% over 1 min, and isocratic elution with 98% B for 9 min. The water and acetonitrile used were of LC-MS grade (Kanto Chemical, Japan). MS/MS conditions were as follows: ion spray voltage floating (kV)=−4.0, desolvation temperature (° C.)=750, collision energy (V)= −30, declustering potential=−90, MS/MS transition (m/z): 349.2/275.2 ([$^2H_2$] $GA_1$), 347.2/273.2 ($GA_1$), 333.2/259.2 ([$^2H_2$] $GA_4$), 331.2/257.2 ($GA_4$). The retention time of GA1 and GA4 on LC were 3.5 min and 6.6 min, respectively. The levels of GAs were determined using a calibration curve ($R^2$>0.997), which was obtained on each occasion by injecting a series of standard solutions (10 μL) that contained a fixed concentration of [$^2H_2$] GAs (50 pg/μL) and varying concentrations of unlabeled GAs (0.5-100 pg/μL). We used a software tool (MultiQuant 2.0, AB SCIEX) to calculate GA concentrations from the LC-MS-MS data.

New high confidence direct LFY targets are known in the art and publicly available in the published transcriptome and ChIP-chip datasets.

TABLE 1

Primers used in this study.

| Primer name | Sequence (5'→3') | SEQ ID NO |
|---|---|---|
| *Primers used for cloning* | | |
| pELA1/gELA-FW | GGGGACAAGTTTGTACAAAAAAGCAGGCTACAGAAACAGCAAGAGCTTTT | SEQ ID NO: 5 |
| pELA1-RV | GGGGACCACTTTGTACAAGAAAGCTGGGTTTTTCTTATCTTTCTTTTTCTT | SEQ ID NO: 6 |
| gELA1/ELA1ox-RV | GGGGACCACTTTGTACAAGAAAGCTGGGTTATATTGTCTCAGAACTCTAAT | SEQ ID NO: 7 |
| ELA1ox-FW | GGGGACAAGTTTGTACAAAAAAGCAGGCTACATGGAGAATTTTATGGTAG | SEQ ID NO: 8 |
| pLFY-FW | GGATCCATTTTTCGCAAAGG | SEQ ID NO: 9 |
| pLFY-RV | AATCTATTTTCTCTCTCTC | SEQ ID NO: 10 |
| RGL1/rgl1-FW | CTGCAGATGAAGAGAGAGCACAACCA | SEQ ID NO: 11 |
| RGL1/rgl1-RV | GTCGACTTATTCCACACGATTGATTC | SEQ ID NO: 12 |
| pLFYGW-FW | GGGGACAAGTTTGTACAAAAAAGCAGGCTACGGATCCATTTTTCGCAAGGA | SEQ ID NO: 13 |
| RGL1/rgl1GW-RV | GGGGACAAGTTTGTACAAAAAAGCAGGCTATGAAGAGAGAGCACAACCA | SEQ ID NO: 14 |
| *Primers used for genotyping* | | |
| ela1-1-LP | ATGGAGAATTTTATGGTAG | SEQ ID NO: 15 |
| ela1-1-RP | ATCTCCCACACATTCCCTTTC | SEQ ID NO: 16 |
| ela1-2-LP | TGGCGAAAACAATACGGTAAG | SEQ ID NO: 17 |
| ela1-2-RP | TGATGGCCTTTTGAAGACATC | SEQ ID NO: 18 |
| ela1-3-LP | ATGGAGAATTTTATGGTAG | SEQ ID NO: 19 |
| ela1-3-RP | ATCTCCCACACATTCCCTTTC | SEQ ID NO: 20 |
| LBb1.3 | ATTTTGCCGATTTCGGAAC | SEQ ID NO: 21 |
| pSKTAIL-L3 | ATACGACGGATCGTAATTTGTCG | SEQ ID NO: 22 |
| *Primers used for mutagenesis* | | |
| pELALFYm1,2 | AATAAGAGGGACCAAGCTTTAGAAAAAGAG | SEQ ID NO: 23 |
| pELALFYm3,4 | GTGTATGGAAAGCTTGACAAATTAAATGTATAGGTAGAAAGCTTGGCTACAG | SEQ ID NO: 24 |
| *Primers used for in situ hybridization* | | |
| ELA1-FW | TGGTAGAGATGGCCAAGACC | SEQ ID NO: 25 |
| ELA1-RV | GGACGAATGACTGAGGGTGT | SEQ ID NO: 26 |

TABLE 1-continued

Primers used in this study.

| Primer name | Sequence (5'→3') | SEQ ID NO |
|---|---|---|
| Primers used for qRT-PCR | | |
| ELA1-FW | TCCGCGATGAAGTCTTTCTT | SEQ ID NO: 27 |
| ELA1-RV | TTGTGTCCTCAAGGGCTTCT | SEQ ID NO: 28 |
| ELA1(upstream)-FW | TGGTAGAGATGGCCAAGACC | SEQ ID NO: 29 |
| ELA1(upstream)-RV | ATTGCTCCGCCATCACTTTA | SEQ ID NO: 30 |
| ELA1(flanking)-FW | GCGAAAACAATACGGGAGAG | SEQ ID NO: 31 |
| ELA1(flanking)-RV | AACTCCGGGTGGTTCATGT | SEQ ID NO: 32 |
| GA20ox2-FW | CTCCGGCAGAGAAAGAACAC | SEQ ID NO: 33 |
| GA20ox2-RV | CCCAATTCGAAAAGGAATCG | SEQ ID NO: 34 |
| AP1-FW | GAAGGCCATACAGGAGCAAA | SEQ ID NO: 35 |
| AP1-RV | ACTGCTCCTGTTGAGCCCTA | SEQ ID NO: 36 |
| TUB 2-FW | AGCAATACCAAGATGCAACTGCG | SEQ ID NO: 37 |
| TUB 2-RV | TAACTAAATTATTCTCAGTACTCTTCC | SEQ ID NO: 38 |
| EIF4-FW | AAACTCAATGAAGTACTTGAGGGACA | SEQ ID NO: 39 |
| EIF4-RV | TCTCAAAACCATAAGCATAAATACCC | SEQ ID NO: 40 |
| Primers for yeast one hybrid | | |
| pAP1-FW | TTCAGTGAGCTCGGGTTCTCACCTTATTCCAAAA | SEQ ID NO: 41 |
| pAP1-RV | CATCGACTCGAGAGGATTTGCGTGTCGACTTC | SEQ ID NO: 42 |
| SPL9-FW | GGGGACAAGTTTGTACAAAAAAGCAGGCTACATGGAGATGGGTTCCAACTC | SEQ ID NO: 43 |
| SPL9-RV | GGGGACCACTTTGTACAAGAAAGCTGGGTTTCAGAGAGACCAGTTGGTAT | SEQ ID NO: 44 |
| RGA-FW | GGGGACAAGTTTGTACAAAAAAGCAGGCTATGAAGAGAGATCATCACCA | SEQ ID NO: 45 |
| RGA-RV | GGGGACCACTTTGTACAAGAAAGCTGGGTTCAGTACGCCGCCGTCGAGA | SEQ ID NO: 46 |
| Primers used for ChIP-qPCR | | |
| AP1-a-F | TCGAACGTGGTGGTTAGAAG | SEQ ID NO: 47 |
| AP1-a-R | CGCAGCAGCTAGCATCTATTT | SEQ ID NO: 48 |
| AP1-b-F | CAAACCTTCCTGCCTTCTTTT | SEQ ID NO: 49 |
| AP1-b-R | AATATCTCGATCCACTAAGATACGG | SEQ ID NO: 50 |
| AP1-c-F | GCAAATGCCGAATCTGTTTT | SEQ ID NO: 51 |
| AP1-c-R | AAAACCTTTGCTCAATTTGC | SEQ ID NO: 52 |
| AP1-d-F | ACACTTGGGGAAGGACCAGT | SEQ ID NO: 53 |
| AP1-d-R | ATGTCGGGTCCATGATTTTT | SEQ ID NO: 54 |
| AP1-e-F | AATGTGTCGCATCTAAGAAGATTT | SEQ ID NO: 55 |
| AP1-e-R | TCGAGTTCTAACTGCGGTTTC | SEQ ID NO: 56 |
| pELA1(transgene)-F | TGTTTGGTCAAAAGGATAGTGC | SEQ ID NO: 57 |
| pELA1(transgene)-R | GCGGGATATCACCACTTTGT | SEQ ID NO: 58 |

TABLE 1-continued

Primers used in this study.

| Primer name | Sequence (5'→3') | SEQ ID NO |
|---|---|---|
| EIF4-FW | TGTTTTGCTTCGTTTCAAGGA | SEQ ID NO: 59 |
| EIF4-RV | GCATTTTCCCGATTACAAC | SEQ ID NO: 60 |

Example 2

Generating Transgenic Corn, Rice, Wheat, Cotton, Soybean, Peanut, Mustard, Rapeseed/Canola, Cabbage, Cauliflower, and Tomatoes Constructs can be prepared by the methods well known in the art. Constructs can include a gibberellin inhibitor (e.g., ELA1) under the control of a flower primordium specific promoter or a lateral organ primordium specific promoter (e.g., LFY promoter). Constructs can also include a gibberellin activator (e.g., GA 20-oxidase) under the control of a vegetative stage specific promoter (e.g., FLC promoter). Reporters such as GUS and/or GFP can also be included in the constructs. The constructs can be cloned into one or more binary vectors (e.g., Gateway binary vector pGWB4 or pBGWF7). The vectors can then be transformed into tissues of corn, rice, wheat, cotton, soybean, peanut, mustard, rapeseed/canola, cabbage, cauliflower, and tomatoes. The aforementioned gibberellin activator or gibberellin inhibitor could be provided constitutively from a tissue-specific promoter or inducibly as described herein or by using methods known in the art.

Transgenic plants are raised. The plants can be tested using the routine methods to determine whether the transgenic molecules are stably integrated into the genome.

The plants can also be tested to determine whether the transgenic molecules are effective in inducing floral fate and other related phenotypic traits. Plants can be grown to obtain seeds.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A recombinant nucleic acid molecule for producing flower formation, said nucleic acid molecule comprising: a transgenic nucleic acid sequence comprising a sequence encoding a floral fate inducer operably linked to a promoter specific to flower primordium or lateral organ primordium, wherein said floral fate inducer is a gibberellin catabolism enzyme, and wherein the promoter specific to flower primordium or lateral organ primordium is heterologous to the nucleic acid sequence encoding the floral fate inducer; and wherein said promoter specific to flower primordium or lateral organ primordium is LFY promoter, ANT promoter, FIL promoter, FD promoter, BRANCHED promoter, AP1/FUL clade promoter, MP promoter, TMO3 promoter, WOX promoter, Indeterminate promoter, RS promoter, rice APO1 promoter, tomato AN promoter, maize ZFL1 promoter or maize ZFL2 promoter.

2. The molecule of claim 1, wherein said promoter is inducible by an external stimuli.

* * * * *